(12) United States Patent
Klapperich et al.

(10) Patent No.: US 10,768,185 B2
(45) Date of Patent: Sep. 8, 2020

(54) TENOFOVIR DETECTION ASSAY

(71) Applicant: TRUSTEES OF BOSTON UNIVERSITY, Boston, MA (US)

(72) Inventors: Catherine M. Klapperich, Brookline, MA (US); George Woodman Pratt, IV, Everett, MA (US); Andy Fan, Cambridge, MA (US)

(73) Assignee: TRUSTEES OF BOSTON UNIVERSITY, Boston, MA (US)

( * ) Notice: Subject to any disclaimer, the term of this patent is extended or adjusted under 35 U.S.C. 154(b) by 0 days.

(21) Appl. No.: 16/040,994

(22) Filed: Jul. 20, 2018

(65) Prior Publication Data
US 2019/0025334 A1   Jan. 24, 2019

Related U.S. Application Data

(60) Provisional application No. 62/534,925, filed on Jul. 20, 2017.

(51) Int. Cl.
*G01N 33/94* (2006.01)
*C07K 16/44* (2006.01)
*G01N 33/558* (2006.01)

(52) U.S. Cl.
CPC ............. *G01N 33/94* (2013.01); *C07K 16/44* (2013.01); *G01N 33/558* (2013.01)

(58) Field of Classification Search
CPC ................................ C07K 16/44; G01N 33/94
See application file for complete search history.

(56) References Cited

U.S. PATENT DOCUMENTS

| | | | |
|---|---|---|---|
| 3,817,837 A | 6/1974 | Rubenstein | |
| 3,850,752 A | 11/1974 | Schuurs | |
| 3,939,350 A | 2/1976 | Kronick | |
| 3,996,345 A | 12/1976 | Ullman | |
| 4,275,149 A | 6/1981 | Litman | |
| 4,277,437 A | 7/1981 | Maggio | |
| 9,599,609 B2 | 3/2017 | Mehra | |
| 2007/0218486 A1* | 9/2007 | Valdez | C07K 16/44 435/6.16 |
| 2008/0227959 A1 | 9/2008 | Goshal et al. | |
| 2008/0268462 A1* | 10/2008 | Kosmeder | C07D 495/04 435/7.1 |
| 2011/0229906 A1 | 9/2011 | Parkin et al. | |
| 2013/0028920 A1 | 1/2013 | Gurny et al. | |
| 2016/0313323 A1 | 10/2016 | Jakubowicz | |

FOREIGN PATENT DOCUMENTS

| | | |
|---|---|---|
| EP | 1914237 B1 | 6/2014 |
| WO | 2017147186 A1 | 8/2017 |

OTHER PUBLICATIONS

Goodrow et al., "Strategies for Immunoassay Hapten Design," in Immunoanalysis of Agrochemicals; Nelson, J., et al.; ACS Symposium Series, 1995, vol. 586, Chapter 9, pp. 119-139.*
Szurdoki et al., "Important Factors in Hapten Design and Enzyme-Linked Immunosorbent Assay Development," in Immunoanalysis of Agrochemicals; Nelson, J., et al.; ACS Symposium Series, 1995, vol. 586, Chapter 4, pp. 39-63.*
Connoly et al., "Chemical synthesis of oligonucleotides containing a free sulphydryl group and subsequent attachment of thiol specific probes," Nucleic Acids Res., 1985, vol. 13, issue 12, pp. 4485-4502.*
A printout retrieved on Feb. 6, 2019 from https://en.wikipedia.org/wiki/Phosphonate.*
Afshar et al., "Comparison of competitive ELISA, indirect ELISA and standard AGID tests for detecting blue-tongue virus antibodies in cattle and sheep", Vet Rec 124(6) 136-141 (1989).
Calcagno et al., "Clinical pharmacology of tenofovir clearance: a pharmacokinetic/pharmacogenetic study on plasma and urines", The Pharmacogenomics Journal 16: 514-518 (2016).
Cheng et al., "Sensitive detection of small molecules by competitive immunomagnetic-proximity ligation assay", Anal Chem 84(5) 2129-2132 (2012).
Perrett et al., "Evaluation of competitive ELISA for detection of antibodies to Brucella infection in domestic animals", Croat Med 51(4) 314-319 (2010).
Cote et al., "Generation of human monoclonal antibodies reactive with cellular antigens", Proc Natl Acad Sci USA 80 (7) 2026-2030 (1983).
Huse et al., "Generation of a large combinatorial library of the immunoglobulin repertoire in phage lambda", Science 246(4935) 1275-1281 (1989).
Karu et al., "Synthesis of Haptens and Derivation of Monoclonal Antibodies for Immunoassay of the Phenylurea Herbicide Diuron", J Agri Food Chem 42(2) 301-309 (1994).
Koenig et al., "Urine assay for tenofovir to monitor adherence in real time to tenofovir disoproxil fumarate/emtricitabine as pre-exposure prophylaxis", HIV Med 18(6) 412-418 (2017).
Kohler et al., "Continuous cultures of fused cells secreting antibody of predefined specificity", Nature 256(5517) 495-497 (1975).
Kumar et al., "Quantification of serum 1-84 parathyroid hormone in patients with hyperparathyroidism by Immunocapture in situ digestion liquid chromatography-tandem mass spectrometry", Clin Chem 56(2) 306-313 (2010).
Simiele et al., "A LC-MS method to quantify tenofovir urinary concentrations in treated patients", J Pharm Biomed Anal 114: 8-11 (2015).
Varal et al., "Synthesis and characterization of Tenofovir disoproxil fumarate impurities, anti HIV drug substance." Der Pharma Chem. 2016, 8 (1), 338-343.

(Continued)

*Primary Examiner* — Galina M. Yakovleva
(74) *Attorney, Agent, or Firm* — Nixon Peabody LLP; Ronald I. Eisenstein; Ravinderjit Braich

(57) ABSTRACT

Disclosed herein are antibodies capable of specifically binding to tenofovir (TFV), a key small molecule drug for both the treatment and prevention of HIV, and a competitive lateral flow assay that uses these antibodies to monitor urine samples for the presence of the drug. The assay can be deployed as a point-of-care device for adherence monitoring.

18 Claims, 17 Drawing Sheets

(56) References Cited

OTHER PUBLICATIONS

Weltzien et al., "T cell immune responses to haptens. Structural models for allergic and autoimmune reactions", Toxicology 107(2) 141-151 (1996).
World Health Organization, "Adherence to Long-Term Therapies—Evidence for Action", 2003.
Ertekin, O; Ozturk, S.;Ozturk, Z.Z. Sensors (Switzerland) 2016, 16(8), 1-12.
Wittenberg, N. J.; Wootla, B.; Jordan, L. R.; Denic, A.; Warrington, A. E.; Oh, S. H.; Rodriguez, M. Expert Rev. Neurother. 2014,14 (4), 449-463.
Cole, "Monoclonal antibodies." Canadian Family Physician 33: 369 (1987).
Cole, et al. "A strategy for the production of human monoclonal antibodies reactive with lung tumor cell lines." Cancer Research 44(7): 2750-2753 (1984).
Pratt et al., "A competitive lateral flow assay for the detection of tenofovir", Anal Chim Acta1017: 34-40 (2018).
Delhunty et al., "The simultaneous assay of tenofovir and emtricitabine in plasma using LC/MS/MS and isotopically labeled internal standards" J Chromatoqr B Analyt Technol Biomed Life Sci 877(20-21) 1907-1914 (2009).
International Search Report dated Sep. 28, 2018 Cited in Corresponding International Application No. PCT/US2018/043057.

* cited by examiner

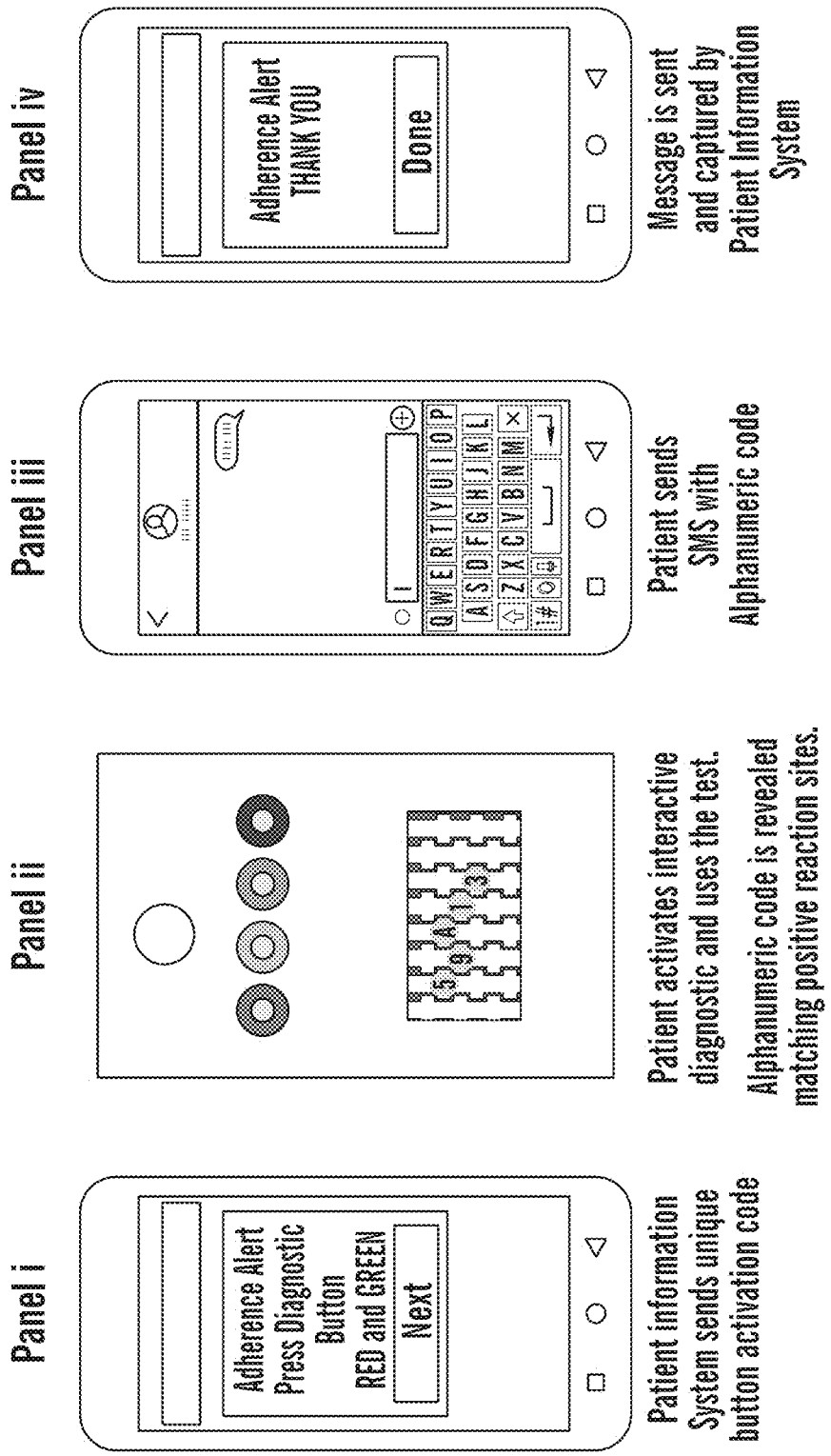

TENOFOVIR DETECTION ASSAY

RELATED APPLICATIONS

This application claims benefit under 35 U.S.C. § 119(e) of the U.S. Provisional Application No. 62/534,925 filed Jul. 20, 2017, the content of which is incorporated herein by reference in its entirety.

GOVERNMENT SUPPORT

This invention was made with Government Support under Contract No. TR001430 awarded by the National Institutes of Health. The Government has certain rights in the invention.

FIELD OF THE INVENTION

This invention relates to antibodies that are capable of specifically binding tenofovir (TFV). The invention further relates to uses of said antibodies, for example detection of TFV in a sample. The invention also relates to devices and methods, such as a competitive lateral flow assay, for the detection of TFV.

BACKGROUND

Tenofovir (TFV) has become a cornerstone of HIV treatment since its approval for use in 2001 as tenofovir disoproxil fumarate (TDF). In 2015 the World Health Organization maintained its recommendation that TDF, which is metabolized into TFV in vivo, be part of the preferred first-line regimen for antiretroviral therapy to treat HIV patients (World Health Organization. Fact Sheet: HIV treatment and care: what's new in HIV treatment; 2015). In addition, the WHO recommends pre-exposure prophylaxis (PrEP) therapies containing TFV-derived medications be deployed to prevent the transmission of the virus among high-risk populations in both high- and low-resource settings (Baggaley, R.; Dalal, S.; Johnson, C.; Macdonald, V.; Mameletzis, I.; Rodolph, M.; Figueroa, C.; Samuelson, J.; Verster, A.; Doherty, M.; Hirnschall, G. J. Int. AIDS Soc. 2016, 19 (1), 21348). As a result of these recommendations and the development of new formulations, such as tenofovir alafenamide (TAF), TFV will likely remain one of the most important tools for the treatment and prevention of HIV.

The number of people accessing antiretroviral medications to manage their HIV infections has risen to over 18 million worldwide as of June 2016 (Joint United Nations Programmed on HIV/AIDS(UNAIDS) Fact Sheet: Global HIV statistics; 2016). Around 10 million of these people are on treatment regimens containing TFV (Clinton Health Access Initiative. ARV Market Report; 2016). With the increasing accessibility and efficacy of these medications it becomes more important to ensure that drug regimens are being properly managed by HIV patients. Mismanagement of HIV drug regimens routinely results in a heightened risk of transmission, decreased patient health and quality of life, and an increase in the incidence of HIV drug resistance (AIDSinfo: Guidelines for the use of antiretroviral agents in HIV-1-infected adults and adolescents; 2017). The WHO cites poor adherence as the main reason for suboptimal clinical benefits managing chronic illnesses such as HIV/AIDS (Dunbar-Jacob, J.; Erlen, J. A.; Schlenk, E. A.; Ryan, C. M.; Sereika, S. M.; Doswell, W. M. Annu. Rev. Nurs. Res. 2000, 18, 48-90). Poor adherence habits have already resulted in a large growth in TFV-resistant HIV strains that threaten to diminish the effectiveness of the drug (The TenoRes Study Group. Lancet Infect. Dis. 2016, 16 (5), 565-575). As a result, it is critical that clinicians monitor the adherence of HIV patients to their prescribed treatment regimens.

To manage HIV infections and keep viral loads low patients must be at least 80-95% adherent to their antiretroviral treatments (Paterson, D. L.; Swindells, S.; Mohr, J.; Brester, M.; Vergis, E. N.; Squier, C.; Wagener, M. M.: Singh, N. Ann. Intern. Med. 2000, 133 (1), 21-30; Montaner, J. S.; Reiss, P.; Cooper, D.; Vella, S.; Harris, M.; Conway, B.; Wainberg, M. A.; Smith, D.; Robinson, P.; Hall, D.; Myers, M.; Lange, J. M. JAMA 1998, 279 (12), 930-937; Bangsberg, D. R.; Hecht, F. M.; Charlebois, E. D.; Zolopa, a R.; Holodniy, M.; Sheiner, L.; Bamberger, J. D.; Chesney, M. a; Moss, a. AIDS 2000, 14 (4), 357-366; Viswanathan, S.; Detels, R.; Mehta, S. H.; Macatangay, B. J. C.; Kirk, G. D.; Jacobson, L. P. AIDS Behav. 2015, 19 (4), 601-611). Studies have shown that many populations of patients do not demonstrate adequate adherence rates (McNabb, J. J.; Nicolau, D. P.; Stoner, J. a; Ross, J. AIDS 2003, 17 (12), 1763-1767; Liu, H.; Golin, C. E.; Miller, L. G.; Hays, R. D.; Beck, C. K.; Sanandaji, S.; Christian, J.; Maldonado, T.; Duran, D.; Kaplan, A. H.; Wenger, N. S.; Inhibitors, H. I. V. P. Ann. Intern. Med. 2001, 134 (10), 968-977; Arnsten, J. H.; Demas, P. A.; Farzadegan, H.; Grant, R. W.; Gourevitch, M. N.; Chang, C. J.; Buono, D.; Eckholdt, H.; Howard, A. A.; Schoenbaum, E. E. Clin. Infect. Dis. 2001, 33 (8), 1417-1423). There are many factors that affect patients and diminish their adherence rates: complexity of regimen, side effects, and patient psychological factors among others (Carr, a. Clin. Infect. Dis. 2000, 30 Suppl 2, S135-42; Chesney, M. A. Improv. Manag. HIV Dis. 1997, 5 (12); Malow R, Devieux J G, Rosenberg R, et al. Psychol AIDS Exch. 2001, 30, 23-26; d'Arminio Monforte, A.; Lepri, A. C.; Rezza, G.; Pezzotti, P.; Antinori, A.; Phillips, A. N.; Angarano, G.; Colangeli, V.; De Luca, A.; Ippolito, G.; Caggese, L.; Soscia, F.; Filice, G.; Gritti, F.; Narciso, P.; Tirelli, U.; Moroni, M. Aids 2000, 14 (5), 499-507; Kaul, D. R.; Cinti, S. K.; Carver, P. L.; Kazanjian, P. H. Pharmacotherapy 1999, 19, 281-298). Fortunately, there are many intervention options available that have been shown to improve adherence behaviors and health outcomes (World Health Organization. Adherence to long-term therapies: Evidence for action; 2003; Vol. 2).

In addition to HIV, tuberculosis (TB) remains a major public health concern more than 60 years after the first effective antibiotics were developed. A prime contributing factor globally to its persistence is inconsistent patient compliance with the 6-9 month first line drug treatment regimen. Non-compliance contributes to morbidity, mortality and rise of multiply drug resistant (MDR) TB. Non-adherence prolongs the infectious state of the disease, leading to more cases. It is more difficult to achieve high adherence in patients with latent TB infection (LTBI) who are not suffering symptoms. Directly Observed Therapy Short-course (DOTS), wherein, the ingestion of each medication dose is observed in-person by healthcare personnel, or more recently over a video feed, is still supported by the WHO as a TB treatment compliance method. However, several studies and meta-analyses conclude that DOTS alone does not increase rates of completion of therapy. While 33% of the world population is infected with the tuberculosis mycobacteria, most of these people will never develop cases of active TB. A small portion of this population, who are at high risk for developing active TB because they have weakened immune systems (due to HIV or other infections), are treated for latent TB each year. Of these, the vast majority receive a monotherapy of isoniazid (INH).

People co-infected with HIV and TB are some of the most vulnerable patients worldwide. TB is the number one cause of death in HIV infected people. HIV patients with LTBI must be treated for both infections and co-infected patients are less likely to adhere to therapy. TB is, for the most part, a curable disease, and HIV can be successfully managed with highly active antiretroviral therapy (ART).

Current methods for tracking adherence behaviors are mostly indirect such as pill counting, electronic drug monitoring, and patient self-reporting (AIDSinfo: Guidelines for the use of antiretroviral agents in HIV-1-infected adults and adolescents.; 2017). Pill counting and electronic monitoring are limited in their deployment and self-reporting, the most widely used method, is prone to overestimation (Waterhouse, D. M.; Calzone, K. A.; Mele, C.; Brenner, D. E. J. Clin. Oncol. 1993, 11 (6), 1189-1197; Gao, X.; Nau, D. P. Ann Pharmacother 2000, 34 (10), 1117-1122). Current direct methods to measure drug levels in patient samples generally require expensive equipment (Simiele, M.; Carcieri, C.; De Nicolò, A.; Ariaudo, A.; Sciandra, M.; Calcagno, A.; Bonora, S.; Di Perri, G.; D'Avolio, A. J. Pharm. Biomed. Anal. 2015, 114, 8-11) that is not easily accessible in resource-limited settings where the need is greatest.

There is therefore a need for compositions, devices and assays that can facilitate objective monitoring of HIV and TB treatment adherence habits in all settings without the need for expensive equipment or long turnaround times allowing clinicians to intervene in cases of noncompliance and improve overall patient outcomes. A cheap and effective monitoring technology that does not rely on health or community workers to see the patient every day and relies on both the provider and the patient to participate, has the potential to provide an effective yet inexpensive method for ensuring compliance.

SUMMARY OF THE INVENTION

The disclosure provides antibodies that can specifically bind with TFV and use of such antibodies in devices and assays for detection/measurement of TFV in a test sample. For example, the antibodies disclosed herein can be used in a competitive lateral flow assay or a dot blot assay for the detection of TFV in a test sample.

TFV, (two forms Tenofovir alafenamide and Tenofovir disproxil fumarate), which is sold under the trade names ATRIPLA, COMPLERA, DESCOVY, GENVOYA, ODEFSEY, STRIBILD, TRUVADA, VEMLIDY, is used to treat chronic hepatitis B, and to prevent and treat HIV and AIDS. As a preventative measure, TFV is administered to patients at high risk of contracting HIV, for example after a needlestick injury. To treat HIV, TFV is administered to a patient having been diagnosed with HIV often in combination with other antiviral medications, for example in combination with emtricitabine, or emtricitabine and efavirenz. TFV is a nucleotide analog reverse-transcriptase inhibitor, and inhibits the capacity for the virus to replicate its RNA genome into double stranded viral DNA. Inhibiting the production of double-stranded viral DNA prevents the virus from multiplying.

Discontinuous dosing of TFV has been shown to result in decreased viral sensitivity to the drug. For example, discontinued use results in severe acute exacerbation of hepatitis B and HIV resistance to TFV. Unfortunately, failure to properly self-administer TFV is common, ranging from 20-57% of patients within 12 months of starting the prescribed treatment. TFV-resistant HIV can also be passed during transmission to another subject and approximately 1% of new HIV infections are resistant to this drug. A complicating condition can be the development of tuberculosis due to the weakened immune system in HIV patients. Inconsistent patient compliance to first line drug treatments such as isoniazid contributes to the morbidity, mortality and rise of drug resistant strains of TB. (Gregson J, Tang M, Ndembi N, Hamers R L, et al. *The Lancet Infectious Disease,* 2016).

Accordingly, the antibodies described herein can be used in methods, assays and devices for detecting presence of TFV in a test sample, for compliance with TFV dosing. Generally, the method for detecting presence of TFV in a test sample comprises contacting a test sample with the antibodies and detecting antibodies bound with TFV. Without limitation, the step of detecting antibodies bound with TFV can comprise a competition assay, a sandwich assay, a displacement assay or an electrochemical detection. In some embodiments, the step of detecting antibodies bound with TFV comprises enzyme-linked immunosorbent assay (ELISA). The test sample can be a biological sample. For example, the test sample can be a biological sample from a subject undergoing treatment with TFV or a compound that metabolizes to TFV. In some embodiments, the test sample is a urine sample from a subject undergoing treatment with TFV or a compound that metabolizes to TFV.

In one aspect, the disclosure provides a composition comprising a population of antibodies capable of specifically binding to TFV. As used herein, the term "specifically binding to" or "specific binding" or "specifically binds to" or is "specific for" refers to the binding of an antibody to a target molecule (antigen), e.g., TFV, and means binding that is measurably different from a non-specific interaction (e.g., a non-specific interaction may be binding to bovine serum albumin or casein). Optionally the population of antibodies is produced by immunization of a mammal with TFV conjugated with a protein, for example wherein the TFV conjugated with the protein is thiolated-TFV. Optionally, the protein is serum albumin, such as bovine serum albumin (BSA) or Keyhole Limpet Hemocyanin (KLH).

In some embodiments, at least a portion of the population of antibodies is conjugated with a solid substrate. For example, at least a portion of the population of the antibodies is immobilized on a first surface of a device for detecting presence or absence of TFV in a test sample.

In some embodiments, at least a portion of the population of antibodies is conjugated with a detectable label such as a nanoparticle, quantum dot, an enzyme that produces a color change in the presence of an enzyme substrate or a fluorescent molecule.

In another aspect, provided herein is a device for detecting the presence of TFV in a test sample. Generally, the device comprises a sample pad and a capture zone on a first surface of the device, and wherein the sample pad is in operable fluid communication with the first surface. In some embodiments, the capture zone comprises a population of antibodies immobilized on the first surface, wherein the antibodies are capable of specifically binding TFV. In some other embodiments, the capture zone comprises a capture agent immobilized on the first surface, wherein the capture agent is capable of specifically binding with TFV or anti-TFV antibodies. The device can be used for detecting presence of TFV in a test sample.

The disclosure also provides a kit comprising antibodies and/or a device described herein. Optionally, the kit can further comprise one or more reagents for detection of the population of antibodies capable of specifically binding TFV.

The compositions, methods, kits and devices described herein can be implemented to facilitate objective monitoring of HIV and TB treatment adherence habits. These can optionally be used in a variety of settings without the need for expensive equipment or long turnaround times, allowing clinicians to intervene in cases of noncompliance and improve overall patient outcomes. These can also be used remotely so that effective monitoring does not rely on health or community workers to see the patient every day and relies on both the provider and the patient to participate. In short, these compositions, methods, kits and devices have the potential to provide an effective yet inexpensive method for ensuring compliance to a treatment for HIV and TB.

BRIEF DESCRIPTION OF THE FIGURES

FIG. 12 shows a schematic work flow for use of a coded test.

DETAILED DESCRIPTION

Figure 1:
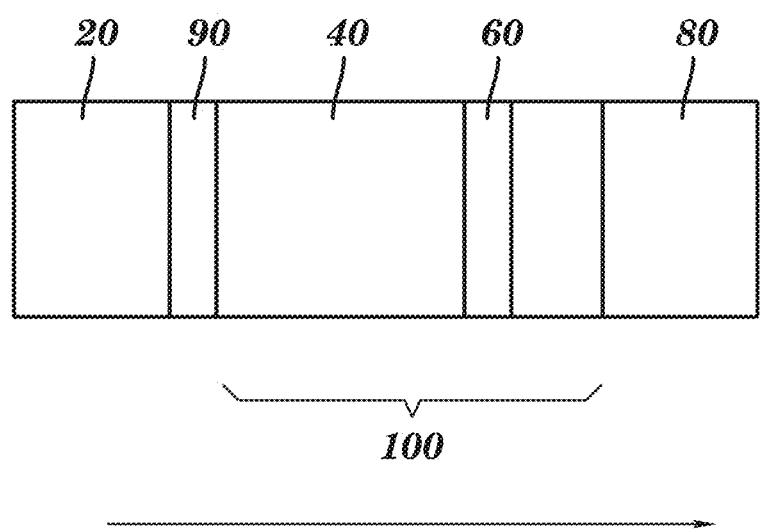
FIG. 1 is a top down highly diagrammatic view of a lateral flow assay strip

The compositions, devices and methods provided herein are based, in part, on the discovery of a population of antibodies capable of specifically binding to TFV and their use for the detection of TFV in a biological sample. Without limitations, these antibodies can allow for the monitoring of patients undergoing treatment with TFV or a TFV prodrug to aid in ensuring patient compliance to a treatment regime.

In one aspect, provided herein is a population of antibodies that are capable of specifically binding with TFV. Without limitation, specific binding can be measured, for example, by determining binding of an antibody to a target molecule compared to binding of antibody to a control molecule. For example, specific binding can be determined by competition with a control molecule that is similar to the target, for example, an excess of non-labeled target. In this case, specific binding is indicated if the binding of the labeled target to a probe is competitively inhibited by excess unlabeled target.

The term "specifically binding to" or "specific binding" or "specifically binds to" or is "specific for" TFV as used herein can be exhibited, for example, by an antibody having a Kd for TFV of at least about 200 nM, alternatively at least about 150 nM, alternatively at least about 100 nM, alternatively at least about 60 nM, alternatively at least about 50 nM, alternatively at least about 40 nM, alternatively at least about 30 nM, alternatively at least about 20 nM, alternatively at least about 10 nM, alternatively at least about 8 nM, alternatively at least about 6 nM, alternatively at least about 4 nM, alternatively at least about 2 nM, alternatively at least about 1 nM, or greater. In certain instances, the term "specific binding" refers to binding where an antibody binds TFV without substantially binding to any other molecule or epitope.

As used herein, the term "binding affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). For example, the Kd can be about 200 nM, 150 nM, 100 nM, 60 nM, 50 nM, 40 nM, 30 nM, 20 nM, 10 nM, 8 nM, 6 nM, 4 nM, 2 nM, 1 nM, or stronger. Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art.

The binding affinity and dissociation rate of an antibody for use in the methods described herein can be determined by any method known in the art. For example, the binding affinity can be measured by competitive ELISAs, RIAs, BIACORE™, or KINEXA™ technology. The dissociation rate also can be measured by BIACORE™ or KINEXA™ technology. The binding affinity and dissociation rate are measured by surface plasmon resonance using, e.g., a BIACORE™, for example, using a BIACORE™-2000 or a BIACORE™-3000 (BIAcore, Inc., Piscataway, N.J.) at 25 C°. with immobilized antigen CMS chips at about 10 response units (RU).

As used herein, the terms "antibody" and "antibodies" refer to intact antibody, or a binding fragment thereof that competes with the intact antibody for specific binding, and include polyclonal antibodies, monoclonal antibodies, humanized or chimeric antibodies, fully human antibodies, bispecific antibodies, single chain Fv antibody fragments, Fab fragments, Fab' fragments, F(ab')$_2$ fragments and F(ab)$_2$ fragments. Antibodies having specific binding affinity for TFV can be produced through standard methods, such as described in the examples section. In some embodiments, binding fragments are produced by recombinant DNA techniques. In additional embodiments, binding fragments are produced by enzymatic or chemical cleavage of intact antibodies. Unless it is specifically noted, as used herein a "fragment thereof" in reference to an antibody refers to an immunospecific fragment, i.e., an TFV-specific or binding fragment.

Without limitations, the antibodies can be monoclonal or polyclonal antibodies. Polyclonal antibodies are heterogeneous populations of antibody molecules that are specific for a particular antigen, which are contained in the sera of the immunized animals. Polyclonal antibodies are produced using well-known methods. A chimeric antibody is a molecule in which different portions are derived from different animal species, such as those having a variable region derived from a murine monoclonal antibody and a human immunoglobulin constant region. Chimeric antibodies can be produced through standard techniques. Antibody fragments that have specific binding affinity for a component of the complex can be generated by known techniques. For example, such fragments include, but are not limited to, F(ab')$_2$ fragments that can be produced by pepsin digestion of the antibody molecule, and Fab fragments that can be generated by reducing the disulfide bridges of F(ab')$_2$ fragments. Alternatively, Fab expression libraries can be constructed. See, for example, Huse et al., 1989, *Science*, 246: 1275. Single chain Fv antibody fragments are formed by linking the heavy and light chain fragments of the Fv region via an amino acid bridge (e.g., 15 to 18 amino acids), resulting in a single chain polypeptide. Single chain Fv antibody fragments can be produced through standard techniques. See, for example, U.S. Pat. No. 4,946,778.

In some embodiments, the antibody or antigen-binding fragment thereof is murine. In some embodiments, the antibody or antigen-binding fragment thereof is from rabbit. In some embodiments, the antibody or antigen-binding fragment thereof is from rat. In other embodiments, the antibody or antigen binding fragment thereof is human. In some embodiments the antibody or antigen-binding fragment thereof is recombinant, engineered, humanized and/or chimeric.

Monoclonal antibodies, which are homogeneous populations of antibodies to a particular epitope contained within an antigen, can be prepared using standard hybridoma technology. In particular, monoclonal antibodies can be obtained by any technique that provides for the production of antibody molecules by continuous cell lines in culture such as described by the human B-cell hybridoma technique (Kohler, G. et al., *Nature*, 1975, 256:495; Kosbor et al., *Immunology Today*, 1983, 4:72; Cole et al., *Proc. Natl. Acad. Sci. USA*, 1983, 80:2026), and the EBV-hybridoma technique (Cole et al., *Monoclonal Antibodies and Cancer Therapy*, Alan R. Liss, Inc., 1983, pp. 77-96). Such antibodies can be of any immunoglobulin class including IgG, IgM, IgE, IgA, IgD, and any subclass thereof. The hybridoma producing the monoclonal antibodies of the invention can be cultivated in vitro or in vivo.

Without wishing to be bound by a theory, antibodies can be produced by immunization of a mammal with TFV conjugated with a protein. As disclosed in the examples herein, the TFV can be thiolated for conjugation with the protein. Exemplary proteins for conjugation include, but are not limited to serum albumin and Keyhole Limpet Hemocyanin (KLH). In some embodiments, serum albumin is bovine serum albumin (BSA).

Conjugation of small molecules, such as TFV to proteins can be accomplished through cross linkers that can react on one end with a protein residue functional group and on the other with a functional group on the small molecule. For example, the cross linkers can form bonds between amines, thiols (e.g., sulfhydryl), carboxyles, carbohydrates and combinations of these. In some embodiments the cross linker is selected to form a link between an amine and a thiol group. For example the cross linker can be N-α-maleimidoacetoxysuccinimide ester (AMAS); N-β-maleimidopropyl-oxysuccinimide ester (BMPS); N-γ-maleimidobutyryl-oxysuccinimide ester (GMBS); sulfo-GMBS; m-maleimidobenzoyl-N-hydroxysuccinimide ester (MBS); sulfo-MBS; (succinimidyl 4-(N-maleimidomethyl)cyclohexane-1-carboxylate (SMCC); sulfo-SMCC; N-ε-malemidocaproyl-oxysuccinimide ester (EMCS); sulfo-EMCS; succinimidyl 4-(p-maleimidophenyl)butyrate (SMPB); sulfo-SMPB; Succinimidyl 6-((beta-maleimidopropionamido)hexanoate)) (SMPH); succinimidyl 4-(N-maleimidomethyl)cyclohexane-1-carboxy-(6-amidocaproate) (LC-SMCC); N-κ-maleimidoundecanoyl-oxysulfosuccinimide ester (Sulfo-KMUS); PEGylated SMCC crosslinkers (e.g., N-hydroxylcussinimide-PEG$_n$-Maleimide with n=2, 4, 6, 8, 12 or 24 ethylene glycol units; succinimidyl 3-(2-pyridyldithio)propionate (SPDP); succinimidyl 6-(3 (2-pyridyldithio)propionamido)hexanoate (LC-SPDP); sulfo-SPDP; 4-succinimidyloxycarbonyl-alpha-methyl-α(2-pyridyldithio)toluene (SMPT); PEGylated, long-chain SPDP crosslinker (e.g., with N-hydroxylsuccinimide-PEG$_n$-2-pyridyldithiol with n=4 and 12); succinimidyl iodoacetate (SIA); succinimidyl 3-(bromoacetamido)propionate (SBAP); succinimidyl (4-iodoacetyl)aminobenzoate (SIAB); and sulfosuccinimidyl (4-iodoacetyl)aminobenzoate (Sulfo-SIAB). For example, an amine group from a lysine residue can be reacted with a cross linker above to form a maleimide activated protein which then can react with a thiol containing molecule.

In some embodiments polyclonal antibodies are produced such as populations obtained from immunization of a mammal (e.g., mouse, rabbit goat, chicken, guinea pigs, hamsters, horses, rats and sheep). In some embodiments the antibodies are produced from rabbits. In some embodiments the antibodies are monoclonal antibodies. In some embodiments the antibodies can be used directly without purification, for example, from polyclonal antibodies harvested from an immunized mammal. In other embodiments the antibodies are purified for example by using a physiochemical fractionation such as by differential precipitation, size-exclusion or solid-phase binding of immunoglobulins based on size, charge or other shared chemical characteristics of antibodies in typical samples. Alternatively, in some embodiments, purification is by class specific affinity which includes a solid phase binding of particular antibody classes (e.g., IgG) by immobilized biological ligands (proteins, lectins, etc.) that have specific affinity to immunoglobulins. Yet another embodiment, purification is by antigen specific affinity which is an affinity purification of only those antibodies in a sample that bind to a particular antigen molecule through their specific antigen-binding domains.

If desired, the antibodies described herein can be conjugated with other components. For example, the antibodies can be immobilized on a surface of various substrates, conjugated with detectable labels, and the like. According to some embodiments of the various aspects disclosed herein, at least a portion of the antibodies in the population is conjugated with or immobilized on a surface of a substrate, such as a solid substrate. The solid substrate can be made from a wide variety of materials and made or incorporated in a variety of formats and structures. For example, the solid substrate can be utilized in the form or structure of, but are not limited to, microparticles or microbeads, nanoparticles or nanobeads, magnetic microbeads and the like, resin beads, nanotubes, fibers, screens, plates, mesh, tubes, hollow fibers, scaffolds, channels in a material, microtiter plates, medical apparatuses (e.g., needles or catheters) or implants, dipsticks or test strips, microchips, filtration devices or membranes, diagnostic strips, hollow-fiber reactors, microfluidic devices, extracorporeal devices, mixing elements (e.g., spiral mixers). Without limitations, the solid substrate can be made of any material, including, but not limited to, metal, metal alloy, polymer, plastic, paper, glass, fabric, packaging material, and any combinations thereof.

In some embodiments, at least a portion of the antibodies in the population is conjugated with or immobilized on a surface of a nanoparticle. Exemplary nanoparticles include, but are not limited to gold nanoparticles and silver nanoparticles.

In some embodiments, at least a portion of the antibodies in the population is conjugated with a detectable label. As used herein, the term "detectable label" refers to a composition capable of producing a detectable signal indicative of the presence of a target. Detectable labels include any composition detectable by spectroscopic, photochemical, biochemical, immunochemical, electrical, optical or chemical means. Suitable labels include fluorescent molecules, radioisotopes, nucleotide chromophores, enzymes, substrates, chemiluminescent moieties, bioluminescent moieties, and the like. As such, a label is any composition detectable by spectroscopic, photochemical, biochemical, immunochemical, electrical, optical or chemical means needed for the methods and devices described herein. Kits for conjugating antibodies with detectable labels are commercially available, for example, from Sigma-Aldrich Corp. (St. Louis Mo.); Thermo Fisher Scientific Inc. (Waltham, Mass.); Fluidigm Corp. (San Francisco, Calif.); Innova Biosciences Ltd. (Cambridge, UK); Abcam (Cambridge, Mass.); Rockland Immunochemicals Inc. (Limerick, Pa.) and GE Healthcare (Chicago, Ill.).

A wide variety of fluorescent reporter dyes are known in the art. Typically, the fluorophore is an aromatic or heteroaromatic compound and can be a pyrene, anthracene, naphthalene, acridine, stilbene, indole, benzindole, oxazole, thiazole, benzothiazole, cyanine, carbocyanine, salicylate, anthranilate, coumarin, fluorescein, rhodamine or other like compound. Exemplary fluorophores include, but are not limited to, 1,5 IAEDANS; 1,8-ANS; 4-Methylumbelliferone; 5-carboxy-2,7-dichlorofluorescein; 5-Carboxyfluorescein (5-FAM); 5-Carboxynapthofluorescein (pH 10); 5-Carboxytetramethylrhodamine (5-TAMRA); 5-FAM (5-Carboxyfluorescein); 5-Hydroxy Tryptamine (HAT); 5-ROX (carboxy-X-rhodamine); 5-TAMRA (5-Carboxytetramethylrhodamine); 6-Carboxyrhodamine 6G; 6-CR 6G; 6-JOE; 7-Amino-4-methylcoumarin; 7-Aminoactinomycin D (7-AAD); 7-Hydroxy-4-methylcoumarin; 9-Amino-6-chloro-2-methoxyacridine; ABQ; Acid Fuchsin; ACMA (9-Amino-6-chloro-2-methoxyacridine); Acridine Orange; Acridine Red; Acridine Yellow; Acriflavin; Acriflavin Feulgen SITSA; Aequorin (Photoprotein); Alexa Fluor 350™; Alexa Fluor 430™; Alexa Fluor 488™; Alexa Fluor 532™; Alexa Fluor 546™; Alexa Fluor 568™; Alexa Fluor 594™; Alexa Fluor 633™; Alexa Fluor 647™; Alexa Fluor 660™; Alexa Fluor 680™; Alizarin Complexon; Alizarin Red; Allophycocyanin (APC); AMC, AMCA-S; AMCA (Aminomethylcoumarin); AMCA-X; Aminoactinomycin D; Aminocoumarin; Anilin Blue; Anthrocyl stearate; APC-Cy7; APTS; Astrazon Brilliant Red 4G; Astrazon Orange R; Astrazon Red 6B; Astrazon Yellow 7 GLL; Atabrine; ATTO-TAG™ CBQCA; ATTO-TAG™ FQ; Auramine; Aurophosphine G; Aurophosphine; BAO 9 (Bisaminophenyloxadiazole); BCECF (high pH); BCECF (low pH); Berberine Sulphate; Beta Lactamase; BFP blue shifted GFP (Y66H); BG-647; Bimane; Bisbenzamide; Blancophor FFG; Blancophor SV; BOBO™-1; BOBO™-3; Bodipy 492/515; Bodipy 493/503; Bodipy 500/510; Bodipy 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy Fl; Bodipy FL ATP; Bodipy Fl-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO™-1; BO-PRO™-3; Brilliant Sulphoflavin FF; Calcein; Calcein Blue; Calcium Crimson™; Calcium Green; Calcium Green-1 $Ca^{2+}$ Dye; Calcium Green-2 $Ca^{2+}$; Calcium Green-5N $Ca^{2+}$; Calcium Green-C18 $Ca^{2+}$; Calcium Orange; Calcofluor White; Carboxy-X-rhodamine (5-ROX); Cascade Blue™; Cascade Yellow; Catecholamine; CFDA; CFP—Cyan Fluorescent Protein; Chlorophyll; Chromomycin A; Chromomycin A; CMFDA; Coelenterazine; Coelenterazine cp; Coelenterazine f; Coelenterazine fcp; Coelenterazine h; Coelenterazine hcp; Coelenterazine ip; Coelenterazine O; Coumarin Phalloidin; CPM Methylcoumarin; CTC; Cy2™; Cy3.1 8; Cy3.5™; Cy3™; Cy5.1 8; Cy5.5™; Cy5™; Cy7™; Cyan GFP; cyclic AMP Fluorosensor (FiCRhR); d2; Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3; DCFDA; DCFH (Dichlorodihydrofluorescein Diacetate); DDAO; DHR (Dihydorhodamine 123); Di-4-ANEPPS; Di-8-ANEPPS (non-ratio); DiA (4-Di-16-ASP); DIDS; Dihydrorhodamine 123 (DHR); DiO (DiOC18(3)); DiR; DiR (DiIC18(7)); Dopamine; DsRed; DTAF; DY-630-NHS; DY-635-NHS; EBFP; ECFP; EGFP; ELF 97; Eosin; Erythrosin; Erythrosin ITC; Ethidium homodimer-1 (EthD-1); Euchrysin; Europium (III) chloride; Europium; EYFP; Fast Blue; FDA; Feulgen (Pararosaniline); FITC; FL-645; Flazo Orange; Fluo-3; Fluo-4; Fluorescein Diacetate; Fluoro-Emerald; Fluoro-Gold (Hydroxystilbamidine); Fluor-Ruby; FluorX; FM 1-43™; FM 4-46; Fura Red™ (high pH); Fura-2, high calcium; Fura-2, low calcium; Genacryl Brilliant Red B; Genacryl Brilliant Yellow 10GF; Genacryl Pink 3G; Genacryl Yellow 5GF; GFP (S65T); GFP red shifted (rsGFP); GFP wild type, non-UV excitation (wtGFP); GFP wild type, UV excitation (wtGFP); GFPuv; Gloxalic Acid; Granular Blue; Haematoporphyrin; Hoechst 33258; Hoechst 33342; Hoechst 34580; HPTS; Hydroxycoumarin; Hydroxystilbamidine (FluoroGold); Hydroxytryptamine; Indodicarbocyanine (DiD); Indotricarbocyanine (DiR); Intrawhite Cf; JC-1; JO-JO-1; JO-PRO-1; LaserPro; Laurodan; LDS 751; Leucophor PAF; Leucophor SF; Leucophor WS; Lissamine Rhodamine; Lissamine Rhodamine B; LOLO-1; LO-PRO-1; Lucifer Yellow; Mag Green; Magdala Red (Phloxin B); Magnesium Green; Magnesium Orange; Malachite Green; Marina Blue; Maxilon Brilliant Flavin 10 GFF; Maxilon Brilliant Flavin 8 GFF; Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); NBD; NBD Amine; Nile Red; Nitrobenzoxadidole; Noradrenaline; Nuclear Fast Red; Nuclear Yellow; Nylosan Brilliant Iavin E8G; Oregon Green™; Oregon Green 488-X; Oregon Green™ 488; Oregon Green™ 500; Oregon Green™ 514; Pacific Blue; Pararosaniline (Feulgen); PE-Cy5; PE-Cy7; PerCP; PerCP-Cy5.5; PE-TexasRed (Red 613); Phloxin B (Magdala Red); Phorwite AR; Phorwite BKL; Phorwite Rev; Phorwite RPA; Phosphine 3R; Photo-Resist; Phycoerythrin B [PE]; Phycoerythrin R [PE]; PKH26; PKH67; PMIA; Pontochrome Blue Black; POPO-1; POPO-3; PO-PRO-1; PO-PRO-3; Primuline; Procion Yellow; Propidium Iodid (PI); PyMPO; Pyrene; Pyronine; Pyronine B; Pyrozal Brilliant Flavin 7GF; QSY 7; Quinacrine Mustard; Resorufin; RH 414; Rhod-2; Rhodamine; Rhodamine 110; Rhodamine 123; Rhodamine 5 GLD; Rhodamine 6G; Rhodamine B 540; Rhodamine B 200; Rhodamine B extra; Rhodamine BB; Rhodamine BG; Rhodamine Green; Rhodamine Phallicidine; Rhodamine Phalloidine; Rhodamine Red; Rhodamine WT; Rose Bengal; R-phycoerythrin (PE); red shifted GFP (rsGFP, S65T); S65A; S65C; S65L; S65T; Sapphire GFP; Serotonin; Sevron Brilliant Red 2B; Sevron Brilliant Red 4G; Sevron Brilliant Red B; Sevron Orange; Sevron Yellow L; sgBFP™; sgBFP™ (super glow BFP); sgGFP™; sgGFP™ (super glow GFP); SITS; SITS (Primuline); SITS (Stilbene Isothiosulphonic Acid); SPQ (6-methoxy-N-(3-sulfopropyl)-quinolinium); Stilbene; Sulphorhodamine B can C; Sulphorhodamine G Extra; Tetracycline; Tetramethylrhodamine; Texas Red™; Texas Red-X™ conjugate; Thiadicarbocyanine (DiSC3); Thiazine Red R; Thiazole Orange; Thioflavin 5; Thioflavin S; Thioflavin TCN; Thiolyte; Thiozole Orange; Tinopol CBS (Calcofluor White); TMR; TO-PRO-1; TO-PRO-3; TO-PRO-5; TOTO-1; TOTO-3; TriColor (PE-Cy5); TRITC (TetramethylRodamineIsoThioCyanate); True Blue; TruRed; Ultralite; Uranine B; Uvitex SFC; wt GFP; WW 781; XL665; X-Rhodamine; XRITC; Xylene Orange; Y66F; Y66H; Y66W; Yellow GFP; YFP; YO-PRO-1; YO-PRO-3; YOYO-1; and YOYO-3. Many suitable forms of these fluorescent compounds are available and can be used for conjugation with the antibodies.

Other exemplary detectable labels include luminescent and bioluminescent markers (e.g., biotin, luciferase (e.g., bacterial, firefly, click beetle and the like), luciferin, and aequorin), radiolabels (e.g., 3H, 125I, 35S, 14C, or 32P), enzymes (e.g., galactosidases, glucorinidases, phosphatases (e.g., alkaline phosphatase), peroxidases (e.g., horseradish peroxidase), and cholinesterases), and calorimetric labels such as colloidal gold or colored glass or plastic (e.g., polystyrene, polypropylene, and latex) beads. Patents teaching the use of such labels include U.S. Pat. Nos. 3,817,837, 3,850,752, 3,939,350, 3,996,345, 4,277,437, 4,275,149, and 4,366,241, each of which is incorporated herein by reference.

In some embodiments, the detectable label is selected from the group consisting of a nanoparticle, a quantum dot, an enzyme that produces a color change in the presence of an enzyme substrate or a fluorescent molecule. In some further embodiments, the detectable label is horseradish peroxidase or an alkaline phosphatase.

In another aspect, provided herein is a kit comprising the antibodies disclosed herein. In some embodiments, the kit further comprises one or more reagents for detection of the antibodies.

Methods and devices to detect target analytes in samples, particularly biological samples, have taken advantage of the specific interactions between biological molecules, such as the interactions between antigen-antibody (or part of antibody, e.g., Fv), ligand-receptor, enzyme-substrate, binding protein-nucleic acid or aptamer, and hybridization of nucleic acid molecules. These interactions allow for the analyte to be isolated or captured from other components in the sample.

A common type of device that incorporates the use of such biological interactions is a lateral flow assay device or strip assay device. Such assay devices typically comprise a reagent pad that contains a binding partner for the analyte of interest coupled to a detectable label (i.e. labeled conjugates) and a porous membrane on which a capture protein (e.g. antibody or antigen) capable of binding the analyte of interest is immobilized. Labeled conjugates that are commonly used in these types of assay devices are antibodies or antigens coupled to gold nanoparticles or colored latex particles. A liquid sample applied to the device travels by capillary action through the reagent pad where any analyte present in the sample binds to the labeled conjugate forming a complex. The complex continues to migrate through the porous membrane to the region where the capture protein is immobilized at which point the complex of analyte and labeled conjugate will bind to the capture protein. The unreacted sample passes through the immobilized capture protein region without binding. The presence of the analyte is then determined by detecting the labeled conjugate in the capture region of the device (e.g. by a color change).

Accordingly, in another aspect provided herein is a device for detecting presence or absence of TFV in sample. Generally, the device comprises a capture zone on a first surface of the device and a sample pad, wherein the sample pad is in operable fluid communication with the first surface. The capture zone can comprise a population of antibodies capable of specifically binding TFV immobilized on the first surface. Alternatively, capture zone comprises a capture agent, capable of specifically binding with TFV or anti-TFV antibodies, immobilized on the first surface. Without limitations, the sample pad can contain one or more dried components, such as buffers, detergents, blocking agents, neutralizing agents, accelerants, and any combinations thereof.

The first surface is preferably a porous material. A "porous" material refers to a material containing a plurality of interstices or pores through which liquid easily flows. The porous material can be made from natural or synthetic substances. Suitable porous materials for use in the device of the present invention include, but are not limited to, nitrocellulosic material, polyvinylidene fluoride (PVDF), polyethylene material (e.g. Porex®), nylon, cellulose acetate, polyester material, polyethersulfone (PES) material, or polysulfone material. Other appropriate porous materials that can be used in the inventive devices are known to those skilled in the art. In some embodiments, a non-porous material can be used as a backing for the first surface.

As discussed above, the device comprises a sample pad in fluid communication with the first surface. As used herein, "fluid communication" or "operable fluid communication" refers to the ability of a liquid to flow or travel between two materials or surfaces. Fluid communication can be established between two porous materials or between a porous material and a non-porous material. In the latter situation, the non-porous material can form a channel or conduit by which fluid can flow by capillary action to establish fluid communication between the non-porous material and the porous material. The sample pad can be manufactured from one of several materials, including but not limited to, polyester, polyacrylic, other polymeric materials, or glass fiber.

In some embodiments, the device further comprises an absorbent pad, wherein the sample pad and the absorbent pad are in operable fluid communication with the first surface. Preferably, the first surface is positioned between the sample pad and the absorbent pad. The absorbent can be constructed from cellulose materials or the like. The absorbent pad can function to facilitate the movement of fluids through the device and to remove excess fluid from other components of the device, such as the sample pad and the first surface.

In some embodiments, the device further comprises a reagent pad, wherein the sample pad and the reagent pad are in operable fluid communication with the first surface. The reagent pad can contain one or more reagents capable of forming a complex with TFV. For example, the reagent pad can comprise a population of antibodies capable of specifically binding with TFV. The antibodies can be dried and subsequently deposited on the reagent pad. In some embodiments, the reagent pad is positioned between the sample pad and the first surface. Such a configuration allows for any TFV present in the sample to interact with the antibodies before contacting the capture agent immobilized on the first surface. The reagent pad can be constructed of similar materials as the sample pad and can contain one or more excipients to stabilize the reagents contained therein. Such excipients will depend on the type of reagent deposited on the reagent pad, but can include albumins, caseins, gelatin, or polymeric stabilizers such as polyvinylpyrrolidone or polyvinyl alcohol.

In some embodiments, the device comprises a sample pad, a reagent pad and an absorbent pad, all of which are in operable fluid communication with the first surface.

In some embodiments, the first surface can comprise an accelerant, blocking agent, neutralizing agent, dried buffers, detergents or a combination thereof.

In some embodiments, the device further comprises a control zone in operable fluid communication with the sample pad and the first surface, wherein the control zone is capable of indicating a positive control for the device. The control zone is preferably positioned downstream, a position that is further down the liquid flow path during normal operation then the first surface. One function of the control zone is to ensure that the liquid sample has proceeded completely through its flow path to the end portion of the device. This function serves to eliminate false negative tests due to disruptions in the sample flow path such that the sample does not reach the detecting complex immobilized on the first surface.

In one embodiment, the control zone contains a control capture agent coupled to a detectable entity, wherein the control capture agent binds a substance that is normally present in or is added to the sample being tested. For example, the control capture agent can bind a compound that has been artificially supplied to the sample. This artificially added compound can be added to the sample prior to application of the sample to the device or it can be present on the device prior to adding the sample, for example, dried into the sample pad or reagent pad. For purposes of illustration, a control capture agent can be streptavidin that would bind biotin that had been artificially added to the sample or already present on the sample pad, e.g., dried into the sample pad. In another embodiment, the control zone contains a control capture agent which specifically binds or captures unbound or overflowing (e.g., from capture zone) reagents.

A top down view of an exemplary embodiment of the device is shown in FIG. 1. Component 20 is a sample pad, component 40 is a test line or zone, component 60 is a control line or zone and component 80 is a wick, waste reservoir, or absorbent pad (e.g., see Raphael C. Wong et al., Lateral Flow Immunoassay, Springer 2009). In some embodiments, a conjugate or reagent pad 90 is also included. The bracketed area 100 is the detection zone. In some embodiments area 100 is a first surface. The arrow indicates the direction of flow of the sample/solution. The components can be mounted on a backing material, such as a card having a pressure sensitive adhesive. The backing can provide structural support. The components can all comprise a single material such as a sheet or web of nitrocellulose, PVDF, polyethylene, nylon, cellulose acetate, polyester, polyethersulfone or polysulfone. Alternatively, one or more of the components can be made of different materials. When using the lateral flow assembly, the sample is applied to the sample pad 20, for example using an applicator (e.g., a pipette to drip sample on the sample pad) or it can be dipped in the sample solution (e.g., in a dipstick configuration). In some embodiments the sample pad is simply an area for addition of the sample, in other embodiments the sample pad can function to modify the sample (e.g., to filter out particulate or cells, or modify the pH of the solution) before it flows to other portions of the device. In some embodiments the sample pad can include the sheet or web material previously described, or it can include cellulose, glass fiber, rayon and other filtration media. From the sample pad, the solution flows toward the test strip. In some embodiments, another component is used between the sample pad and test strip known as the conjugate or reagent pad 90. The conjugate pad (e.g., reagent pad) can be used to hold reagents needed in the assay. For example, a labeled antibody can be contained in the conjugate pad until it is contacted with the sample solution, wherein it mixes with the solution and can function as intended (e.g., to bind to an analyte, the antigens in the test line or antibodies in the control line strip). In addition to the sheet or web material previously mentioned, the conjugate pad can comprise glass fibers, polyesters, or rayon. In some embodiments the sample pad 20 and conjugate pad are combined. The test line 40 is functionalized to indicate the presence of the analyte. For example, the test line can be an area or zone functionalized with a specific antibody in a sandwich type assay configuration or with an analyte in a competition assay configuration. The control line 60 is functionalized so that it will indicate that a sample has been applied to the assay. For example, the control line can be functionalized with a non-specific antibody for a sandwich or competition type assay. Both the test line 40 and control line 60 can be configured differently than depicted, for example, as one or more spots. Multiple test lines and control line can also be used, for example, when the test is multiplexed. In some embodiments multiple lines each with different concentrations of the specific antibody, antigen or non-specific antibody can be printed/added to the strip so that different sensitivity regimes can be accessed or the concentration of the analyte can be more accurately estimated/determined. The wick 80 (e.g., waste reservoir or absorbent pad) is designed to pull all the fluid added to the strip into this region and to hold it for the duration of the assay. Thus the wick, in normal operation, causes the material to flow from 20 to 80, e.g., in the direction indicated by the arrow. In addition to the sheet and webbing materials previously mentioned, the wick can be chosen to have a high absorptive capacity such as a high-density cellulose (e.g., chromatograph paper). The lateral flow strip can be enclosed in a housing. The housing can be made of any useful material such as a rigid molded plastic. The housing can have openings, and window access/viewing areas appropriately placed for operation of the device. For example, an opening for application of the sample on the sample pad and openings or windows for viewing or analysis of the test and control strip.

Other configurations of device can also be used. For example, some embodiments do not use a control strip. Some embodiments do not use a conjugate pad 90. In some embodiments, the sample pad, conjugate pad control strip and wick are not used and the test is configured as a dot-blot assay. In the dot blot assay test spots (e.g., dots) are located on a sheet or web and the strip can be completely immersed in the biological solution to be tested.

The sheet and webbing material can be a porous material. For example, the material can have an interconnected porosity so that the materials can wick and flow fluid through them with a constant flow rate. As used herein "webbing" or "web" indicates a flexible material that can be made from polymers or fibrous materials such as a woven or non-woven textile, paper or felt.

One or more of the components of the lateral flow assay device can be treated with one or more of buffers, detergents, blocking agents, neutralizing agents, and accelerants. For example, these can be applied to the sample pad, the detection zone, and/or the wick as a solution and then these agents can be dried thereupon (e.g., by lyophilization).

Some lateral flow assay devices are described in U.S. Pat. No. 9,599,609, content of which is incorporated herein by reference in its entirety.

A kit is any manufacture (e.g., a package or container) comprising reagents useful for monitoring HIV and/or TB treatment adherence, the manufacture being promoted, distributed, or sold as a unit for performing the methods or assays described herein. For example, the kit can include a devise for a lateral flow assay as previously described.

In some embodiments, a kit comprises reagents including anti-TFV antibodies that can be conjugated (e.g., to nanoparticles). The anti-TFV antibodies can be provided in a solution the can be diluted or one or more pre-diluted solutions containing the antibody can be provided. The kit can also include other reagents such as dyes or pre dyes such as barbituric acid and thiocyanogen chloride. The pre dye can be supplied in solution and in one or more concentrations. The regents can also include blocking agents, neutralizing agents, accelerants, buffers and detergents. The kit can also include an oxidizer such as hydrogen peroxide and chromogenic compounds such as 3,3',5,5'-Tetramethylbenzidine (TMB). The kit can also include a lateral flow assay device as previously described.

The kit can include a container such as a cup for sample collection and/or dipping a test strip (e.g., dipstick) therein. The kit can include a method for stirring the sample and any of the required reagents. For example, the container can include a sealable lid so the container can be shaken or can include a stirrer such as a stirring stick. A kit can include indicators or labels, for example to indicate a sample has been collected and any other information (e.g. a sample number, name, date etc. . . . ). The Kit can include disinfectants and barrier devices for safe handling of samples (e.g., gloves). For example, the disinfectant can be used for wiping down the sample container after use, or the disinfectant can be a disinfectant that is added to the sample (e.g., a disinfectant that does not interfere with the test). For example, the disinfectant can be diluted bleach, alcohol or any other known disinfectant. The kit can also include an applicator such as a pipette for applying the sample to a flow strip. The kit can also include items for waste disposal such as disinfectants and sealable containers (e.g., bags) with biological waste labels.

The components of a kit can be retained by a container. Instructions for using the kit to perform a described method can be provided with the container, and can be provided in any fixed medium. The instructions can be located inside the container or outside the container, and can be printed on the interior or exterior of any surface forming the container that renders the instructions legible. Instructions can also be printed on items in the container, such as on the lateral flow assay device. A kit can be in multiplex form for detection of one or more different target drugs (e.g., TFV or INA), optionally having more than one dipstick, dotblot assay strip, reagents.

When the kits, and methods described herein are used for detection of HIV and/or TB drugs the drug detection probes or systems can be selected such that a positive result is obtained in at least about 20%, at least about 40%, at least about 60%, at least about 80%, at least about 90%, at least about 95%, at least about 99% or in 100% of subjects who have taken the prescribed drugs according their prescription regime.

Embodiments of the invention can also be described by any one of the following numbered paragraphs.

1. A composition comprising a population of antibodies capable of specifically binding tenofovir (TFV).
2. The composition of paragraph 1, wherein the population of antibodies is produced by immunization of a mammal with TFV conjugated with a protein.
3. The composition of paragraph 2, wherein the conjugated TFV is thiolated TFV.
4. The composition of paragraph 1 or 2, wherein the protein is albumin or Keyhole Limpet Hemocyanin (KLH).
5. The composition of any one of paragraphs 1-4, wherein the serum albumin is bovine serum albumin (BSA).
6. The composition of any one of paragraphs 1-5, wherein said composition is configured for detection of TFV in a test sample.
7. The composition of any one of paragraphs 1-6, wherein said composition is configured for detection of TFV in a test sample via a competition assay, a sandwich assay, a displacement assay or an electrochemical detection.
8. The composition any one of paragraphs 1-7, wherein at least a portion of the population of antibodies is conjugated to a solid substrate.
9. The composition of any one of paragraphs 1-8, wherein the solid substrate is a nanoparticle.
10. The composition of any one of paragraphs 1-9, wherein the solid substrate is a gold or silver nanoparticle.
11. The composition of any one of paragraphs 1-10, wherein at least a portion of the population of antibodies is immobilized on a first surface of a detection device comprising a sample pad, and wherein
the sample pad is in operable fluid communication with the first surface.

12. The composition of any one of paragraphs 1-11, wherein at least a portion of the population of antibodies is conjugated with a detectable label.
13. The composition of paragraph 12, wherein the detectable label is a nanoparticle, quantum dot, an enzyme the produces a color change in the presence of an enzyme substrate, or a fluorescent molecule.
14. The composition of paragraph 13, wherein the enzyme is horseradish peroxidase, an alkaline phosphatase, or any combination thereof
15. A kit comprising a composition of any one of paragraphs 1-14.
16. The kit of paragraph 15, further comprising a reagent for detection of the population of antibodies capable of specifically binding TFV.
17. A device for detecting the presence of TFV in a sample, comprising:

a sample pad; and a population of antibodies capable of specifically binding TFV immobilized on a first surface; and wherein the sample pad is in operable fluid communication with the first surface.
18. The device of paragraph 17, wherein the first surface is a porous surface.
19. The device of paragraph 17 or 18, wherein the first surface comprises nitrocellulosic material, polyvinylidene fluoride (PVDF), polyethylene material, nylon, cellulose acetate, polyester material, polyethersulfone (PES), or polysulfone.
20. The device as in any one of paragraphs 17-19, wherein the sample pad or the first surface, or both, comprises an accelerant, a blocking agent, a neutralizing agent, or a combination thereof.
21. The device as in any one of paragraphs 17-20, wherein the sample pad comprises one or more dried buffers or detergents or a combination thereof.
22. The device as in any one of paragraphs 17-21, further comprising an absorbent pad that is in operable fluid communication with the first surface.
23. The device as in any one of paragraphs 17-20, further comprising a reagent pad that is in operable fluid communication with the first surface.
24. The device as in any one of paragraphs 17-20, further comprising a reagent pad and an absorbent pad both of which are in operable fluid communication with the first surface.
25. The device as in any one of paragraphs 17-24, further comprising a control zone in operable fluid communication with the sample pad, reagent pad and the first surface, wherein the control zone is capable of indicating a positive control for the device.
26. The device of any one of paragraphs 17-25, wherein the device is positioned in an enclosed housing.
27. A method of detecting TFV in a test sample, comprising:

contacting the test sample with the sample pad of the device of any one of paragraphs 17-26; and detecting binding of TFV with said antibodies.
28. The method of paragraph 27, wherein the test sample is a biological sample.
29. The method of paragraph 28, wherein the biological sample is urine.
30. A device for detecting presence of TFV in a sample, comprising:

a sample pad; and a capture agent immobilized on a first surface, wherein the capture agent is capable of specifically binding with anti-TFV antibodies; and wherein the sample pad is in operable fluid communication with the first surface.
31. The device of paragraph 30, wherein said capture agent is an antibody.
32. The device of paragraph 30 or 31, wherein the first surface is a porous surface.
33. The device of any one a paragraphs 30-32, wherein the first surface comprises nitrocellulosic material, polyvinylidene fluoride (PVDF), polyethylene material, nylon, cellulose acetate, polyester material, polyethersulfone (PES), or polysulfone.
34. The device as in any one of paragraphs 30-33, wherein the sample pad or the first surface, or both, comprises an accelerant, a blocking agent, a neutralizing agent, or a combination thereof.
35. The device as in any one of paragraphs 30-34, wherein the sample pad comprises one or more dried buffers or detergents or a combination thereof.
36 The device as in any one of paragraphs 30-35, further comprising an absorbent pad that is in operable fluid communication with the first surface.
37. The device as in any one of paragraphs 30-35, further comprising a reagent pad that is in operable fluid communication with the first surface.
38. The device as in any one of paragraphs 30-35, further comprising a reagent pad and an absorbent pad both of which are in operable fluid communication with the first surface.
39. The device as in any one of paragraphs 30-38, further comprising a control zone in operable fluid communication with the sample pad, reagent pad and the first surface, wherein the control zone is capable of indicating a positive control for the device.
40. The device of any one of paragraphs 30-39, wherein the device is positioned in an enclosed housing.
41. A method of detecting TFV in a test sample: comprising:

contacting the test sample with the sample pad of the device of any one of paragraphs 30-40, and detecting binding of said capturing agent with TFV bound with an anti-TFV antibody.
42. The method of paragraph 41, wherein the test sample is a biological sample.
43. The method of paragraph 42, wherein the biological sample is urine.
44. An assay for detecting the presence of tenofovir in a biological sample, comprising:

(i) contacting a biological sample with a composition of any one of paragraphs 1-14, wherein the biological sample is from a subject undergoing treatment with TFV or a compound that metabolizes to TFV; and (ii) detecting binding of antibodies bound with tenofovir.
45. The assay of paragraph 44, wherein the said detection comprising a competition assay, a sandwich assay, a displacement assay or an electrochemical detection.

46. The assay of paragraph 44 or 45, wherein said detection comprises enzyme-linked immunosorbent assay (ELISA).
47. The assay of any one of paragraphs 44-46, wherein the assay is a dipstick assay.

Definitions

As used herein "conjugation" forms a link between molecules, polymers, particles, and surfaces of bulk materials (e.g., a web or sheet made with nitrocellulose, PVDF, polyethylene, nylon, cellulose acetate, polyester, polyethersulfone or polysulfone) and combinations of these. For example, conjugation can be between a molecule and a polymer, a molecule and a particle, a polymer and a particle, a molecule and a surface, a polymer and a surface, or between two molecules. For example, "bioconjugation" forms a stable link between two molecules, at least one of which is a biomolecule such as a protein. For example, bioconjugation can be between a protein and a drug, such as TFV conjugation with BSA or KLH. Bioconjugatinon can be between a protein and a particle such as between an antibody (e.g., anti-TFV antibody) and gold, silver, quantum dots or mono-dispersed latex particles. The link can be by covalent bonding, electrostatic interactions, hydrogen bonding or weaker interactions such as dipole-dipole interactions or Van Der Waals interactions, or combinations of these.

As used herein "thiolated" refers to formation of a pendant thiol group on a molecule. For example, the thiol group can be formed at any point on the molecule and have a chain or linking group to the molecule. The bonding of the chain or linking group to the molecule can be a covalent bond, an ionic bond or a weak boding interaction. In some embodiments the chain is linked by a covalent bond. For example, bonding in some embodiments is accomplished by a condensation reaction of a phosphate group with an alcohol of a bi-functional mercapto-alcohol containing molecule forming a phosphonate ester having a pendent thiol group. For example, the bi-functional molecule can be 2-mercaptoethanol, 3-mercaptopropanol 3-mercapto-1-propanol, 4-mercapto-1-butanol or any compound having the formula HS-$(CH_2)_n$-OH where n is selected between 2 and 20 (e.g., n=1, 2, 3, 4, 5, 6, 7, 8, 9, 10, 11, 12, 13, 14, 15, 16, 17, 18, 19, 20). The carbon chain can be replaced with other chains including, for example, heteroatoms such a PEG chain.

As described herein a "competition assay" is one where the analyte competes with a non-analyte for binding and this competition can be detected, for example, by loss of the non-analyte from the binding site. For example, an unlabeled analyte in a sample competes with labeled analyte to bind with an antibody conjugated to a surface. The amount of antibody-labeled analyte present after the test is inversely related to the amount of antibody-unlabeled analyte. If the detection method detects the antibody-labeled antibody, then the signal is inversely related to the amount of analyte in the sample. In an alternative, a selective labeled antibody competes for analyte that is in solution and an analyte that is conjugated to a surface. The amount of signal is again inversely proportional to the amount of analyte in solution if the surface bound analyte is interrogated after the test. An art know competitive assay is the competitive ELISA assays.

As described herein a "sandwich" assay is an assay wherein a specific capture agent (e.g., a capture or specific antibody) binds to an analyte (e.g., selectively). A second specific antibody is added that can bind to the analyte forming the "sandwich". The second antibody is detected either directly (e.g., by being labeled) or by a secondary antibody that can be detected. For example, a common format used in an ELISA sandwich assay uses a capture antibody conjugated to a surface, where an antigen can bind. A second selective antibody is added to form the "sandwich". A labeled antibody is then added that can be detected. The detection method depends on the labeled antibody. For example, a biotinylated capture antibody that is conjugated through streptavidin with Horseradish peroxidase (HRP) is detectable by electrochemical methods, fluorescence or visually.

As described herein a "displacement" assay is an assay wherein the analyte, when present, dislodges a pre-bound moiety. For example, a ligand displacement immunoassay is an immunoassay that uses an immunocomplex consisting of immobilized antibodies that have been presaturated with labeled analyte ligand, or conversely, it can use a complex of immobilized analyte ligands that are prebound with corresponding labeled antibodies. The complex of antibody—antigens dissociates when it is exposed to analytes. Thus, the labeled reagents are displaced by the analyte in the test sample. In some embodiments the displacement and competition assays can be equivalent, for example, where an unlabeled analyte in a sample competes with a labeled analyte that is bound to a surface (e.g., through a surface conjugated antigen). The unlabeled analyte can displace the labeled analyte from the surface in this competition/displacement assay.

As used herein a "biological" sample is a sample containing one or more biological compounds such as a protein, DNA, fats and metabolites. The biological sample can also include none biological compounds such as pharmaceutical drugs and toxins. The samples can be sourced from patients such as a bodily fluid collected from the patient (e.g., blood, mucus, amniotic fluid, semen, tears, blood plasma, urine, and saliva). The biological sample can be diluted or concentrated and otherwise processed, for example, filtered, buffered to a selected pH, contacted with a labeling compound (e.g., labeled antibody), sterilized (e.g., autoclaved, chemically treated), prior to being subjected to testing. In some embodiments the biological sample is urine.

Assays that include electrochemical detection are also known, for example as described in U.S. patent application Ser. No. 14/784,859 which is herein incorporated by reference.

As used herein a "prodrug" is a medication or compound that, after administration, is metabolized into a pharmacologically active drug. For example, tenofovir disproxil and tenofovir alafenamide fumarate are prodrugs of tenofovir.

As used herein a "blocking agent" or "molecular blockers" are compounds used to prevent non-specific interactions. The blocking agent can be a solution that is applied to a surface to provide a coating on a surface that prevents non-specific interactions or fouling of the surface, for example, when it is contacted with a biological sample. The surface can include a capture agent such as an antibody or an antigen. Non-specific interactions can include any interaction that is not desired between the target molecule and the surface, or between other components in solution. The blocking agent can be a protein, mixture of proteins, fragments of proteins, peptides or other compounds that can passively absorb to the surface in need of blocking. For example, proteins (e.g., BSA and Casein), poloxamers (e.g., pluronics), PEG-based polymers and oligomers (e.g., diethylene glycol dimethyl ether), cationic surfactants (e.g., DOTAP, DOPE, DOTMA). Some other examples include commercially available blocking agent or components therein that are available from, for example, Rockland Inc.

(Limeric, Pa.) such as: BBS Fish Gel Concentrate; PBS Fish Gel Concentrate; TBS Fish Gel Concentrate; ABTS ELISA Peroxidase Substrate; BCIP/NBT Membrane Alkaline Phosphatase Substrate; BCIP/TNBT Membrane Alkaline Phosphatase Substrate; Blocking Buffer for Fluorescent Western Blotting; BLOTTO; Bovine Serum Albumin (BSA); Chemiluminescent FemtoMax™ Super Sensitive HRP Substrate; Chemiluminescent PicoMax™ Sensitive HRP Substrate; DAB Membrane Peroxidase Substrate; ELISA Microwell; Goat Serum; IPTG (isopropyl beta-D-thiogalactoside) Inducer; Normal Goat Serum (NGS); Normal Rabbit Serum; Normal Rat Serum; Normal Horse Serum; Normal Sheep Serum; NPP ELISA Alkaline Phosphatase Substrate; Nitrophenyl phosphate buffer (NPP); Revitablot™ Western Blot Stripping Buffer; TMB ELISA Peroxidase Substrate; and X-GAL Beta-Galactosidase Substrate.

As used herein an "accelerant" is an agent that facilitates the spectral shift of a detecting complex produced by the specific binding of an analyte to the detecting complex. For example, the detecting complex can be an antibody conjugated to a label such as a dye, a fluorophore, an enzyme, a redox active compound, a metal, a quantum dot or a particle that is used for detection. Suitable accelerants include, but are not limited to, polyethylene glycol, polyvinylpyrrolidone, polyvinyl alcohol, other like polymers, and mixtures thereof.

As used herein a "neutralizing agent" is an agent that reduces the chemical reactivity of at least one interfering species. An interfering species can be a biological molecule or other compound present in a sample that exhibits a non-specific binding affinity to the detecting complex. Non-limiting examples of neutralizing agents include alkylating agents, such as iodoacetamide, iodoacetate, N-ethylmaleimide, PEG-maleimide, ethylmethanesulfonate, 4-vinylpyridine, nitrogen mustards, nitrosourea compounds, dacarbazine, and temozolomide.

As used herein a detergent is a surface active compound. Non-limiting examples of suitable detergents that can be used herein are Tween-20, Triton X-100, saponin, zwittergents based on sulfotaines, CHAPS, octyl glucosides, and lauryl sulfates.

Buffers can also be used, for example non-limiting examples of standard buffers are Tris, Hepes, imidazole, or phosphate.

As used herein the term "consisting essentially of" refers to those elements required for a given embodiment. The term permits the presence of elements that do not materially affect the basic and novel or functional characteristic(s) of that embodiment of the claimed invention.

As used herein the term "comprising", "comprises", "including" or "includes" is used in reference to compositions, methods, and respective component(s) thereof, that are essential to the claimed invention, yet open to the inclusion of unspecified elements, whether essential or not.

The term "consisting of" refers to compositions, methods, and respective components thereof as described herein, which are exclusive of any element not recited in that description of the embodiment.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth. Similarly, the word "or" is intended to include "and" unless the context clearly indicates otherwise.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology, and molecular biology can be found in The Merck Manual of Diagnosis and Therapy, 18th Edition, published by Merck Research Laboratories, 2006 (ISBN 0-911910-18-2); Robert S. Porter et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006. Definitions of common terms in molecular biology are found in Benjamin Lewin, Genes IX, published by Jones & Bartlett Publishing, 2007 (ISBN-13: 9780763740634); Kendrew et al. (eds.), The Encyclopedia of Molecular Biology, published by Blackwell Science Ltd., 1994 (ISBN 0-632-02182-9); and Robert A. Meyers (ed.), Maniatis et al., Molecular Cloning: A Laboratory Manual, Cold Spring Harbor Laboratory Press, Cold Spring Harbor, N.Y., USA (1982); Sambrook et al., Molecular Cloning: A Laboratory Manual (2 ed.), Cold Spring Harbor Laboratory Press, Cold Spring Harbor, N.Y., USA (1989); Davis et al., Basic Methods in Molecular Biology, Elsevier Science Publishing, Inc., New York, USA (1986); or Methods in Enzymology: Guide to Molecular Cloning Techniques Vol. 152, S. L. Berger and A. R. Kimmerl Eds., Academic Press Inc., San Diego, USA (1987); Current Protocols in Molecular Biology (CPMB) (Fred M. Ausubel, et al. ed., John Wiley and Sons, Inc.), Current Protocols in Protein Science (CPPS) (John E. Coligan, et. al., ed., John Wiley and Sons, Inc.) and Current Protocols in Immunology (CPI) (John E. Coligan, et. al., ed. John Wiley and Sons, Inc.), which are all incorporated by reference herein in their entireties.

It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims.

All patents and other publications identified are expressly incorporated herein by reference for the purpose of describing and disclosing, for example, the methodologies described in such publications that could be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

This invention is further illustrated by the following examples which should not be construed as limiting.

EXAMPLES

Materials and Methods

TFV was purchased from Ark Pharm, Inc. (Libertyville, Ill.). Bovine serum albumin (BSA), keyhole limpet hemocyanin (KLH), sulfosuccinimidyl 4-(N-maleimidomethyl)cyclohexane-1-carboxylate (sulfo-SMCC), 1-Ethyl-3-(3-dimethylaminopropyl)carbodiimide (EDC), Pierce Protein G agarose beads, CarboxyLink Coupling Gel, Whatman chromatography paper, and pico chemiluminescent substrate were purchased from ThermoFisher (Waltham, Mass.). Amersham Protran nitrocellulose was purchased from GE Healthcare Life Sciences (Pittsburgh, Pa.). Anti-rabbit antibody conjugated to horseradish peroxidase (HRP) was purchased from GE Healthcare (Chicago, Ill.). Goat anti-rabbit antibody was purchased from Abcam (Cambridge, Mass.). N,N'-Dicyclohexylcarbodiimide (DCC), pyridine, 3-mercapto-1-propanol, silica gel Davisil grade 643, Hi-Flow Plus HF180 nitrocellulose sheets, adenosine monophosphate, Tween 20, sucrose, adenosine monophosphate (AMP), and all solvent and buffers were purchased from Sigma-Aldrich (St. Louis, Mo.). 40 nm InnovaCoat Gold Conjugation Kit was purchased from Innova Biosciences (Babraham, England).

Synthesis of Tenofovir-Thiol Hapten

The synthesis of tenofovir-thiol (TFV-SH) was performed using a slightly modified version of the protocol of Varal et al. (Varal, D.; Joshi, M.; Panmand, D.; Jadhav, V. Der Pharma Chem. 2016, 8 (1), 338-343) for the esterification of the tenofovir phosphonate group. In short, 270 mg of TFV and 389 mg of DCC were measured into a round-bottom flask to which 10 mL of dry pyridine and 100 µL of 3-mercapto-1-propanol was added. The mixture was stirred under argon and refluxed for 18-24 hours. The solution was dried and dissolved in 10 mL of a 1:1 dichloromethane:methanol mixture. The solution was filtered and concentrated. Flash chromatography through a short silica gel column was performed on the concentrate. The elution of the column was achieved by a gradient from 0% methanol to 40% methanol in dichloromethane. The fractions of interest were dried by rotary evaporation followed by high vacuum overnight. The presence of TFV-SH was confirmed by liquid chromatography-mass spectrometry (LC-MS).

LC-MS Characterization

LC-MS measurements were taken on an Agilent 1100 series LC/MSD with a Cortecs C18 column (90 Å, 2.7 µm, 4.6 mm×150 mm) from Waters (Milford, Mass.). Samples were dissolved in a solution of 9754, 0.6% trifluoroacetic acid in water and 254, methanol. 204, of sample was injected into a gradient mobile phase outlined in Table 1 at a flowrate of 0.6 mL/min into the column equilibrated at 45° C. and passed through the mass spectrometer set for positive polarity electrospray ionization (ESI+) at a range of 100-1500 m/z.

TABLE 1

Mobile phase gradient for LC-MS detection of TFV, TFV-SH, and AMP.

| Time (Min.) | Water + 0.1% Formic Acid(%) | Acetonitrile + 0.1% Formic Acid(%) |
|---|---|---|
| 0.0 | 100 | 0 |
| 0.5 | 95 | 5 |
| 1.8 | 92 | 8 |
| 3.5 | 90 | 10 |
| 6.0 | 88 | 12 |
| 6.5 | 30 | 70 |
| 9.0 | 30 | 70 |
| 9.5 | 100 | 0 |
| 14.0 | 100 | 0 |

KLH-TFV and BSA-TFV Conjugation 20 mg of BSA and 20 mg of KLH were each dissolved in 2 mL of phosphate buffer saline (PBS). To each protein solution 4 mL of 5 mg/mL sulfo-SMCC in PBS was added. The samples were incubated for 1 hour at room temperature while rotating before being desalted into PBS. 50 mg of TFV-SH was dissolved in 5004, methanol and added to each sample before being incubated for 2 hours at room temperature while rotating. The samples were desalted into PBS. About 3004, of the BSA-TFV sample was then desalted into pure water and conjugation was confirmed by matrix-assisted laser desorption/ionization—time of flight (MALDI-TOF) and acrylamide gel electrophoresis.

Immunoprecipitation of BSA-TFV Conjugate

To a mixture of 250 µL of 1 mg/mL BSA and 250 L of 10 µg/mL diluted BSA-TFV conjugate 1 µL, of serum was added and incubated overnight at 4° C. (+IP sample). A no serum control was prepared as well (-IP sample). 20 µL of the sample was set aside as the "Total" sample. 20 µL Protein-G beads were added to each sample and incubated for 1 hour at 4° C. The samples were spun down for 1 minute at 3000 rpm and decanted. The supernatant from the -IP sample ("Supernatant") was set aside. The beads were then washed and decanted four times with yeast lysis buffer (50 mM HEPES pH 7.6, 1 mM EDTA, 1% Triton X-100, 0.1% sodium deoxycho-late, 140 mM NaCl), with the third wash being with a high salt yeast lysis buffer (500 mM NaCl). The beads were heat eluted and Western blotting was performed with anti-TFV primary antibody and anti-rabbit HRP secondary antibody. Chemiluminescent photographs were taken by a VersaDoc Imaging Model 4000 system from BioRad.

Anti-TFV Antibody Development

Antibody development was conducted by Covance Inc. (Denver, Pa.). This was done in accordance with the NIH guidelines for the care and use of animals in research and under warranty that appropriate IRB approval was obtained. KLH-TFV was injected into rabbits and the serum containing anti-TFV polyclonal antibodies was collected and used for the current study.

Immunoprecipitation of TFV by Anti-TFV Antibody

Two samples were prepared containing a mixture of 1004, of 50 µg/mL TFV and 100 µL of 1 mg/mL AMP. To one tube 375 µL of anti-TFV serum (+IP) was added and to the other 375 µL of PBS (-IP). The samples were incubated while rotating at 4° C. overnight. 3004, of Protein G bead suspension was added to the samples and further incubated at 4° C. for 1 hour. The samples were spun down for 1 minute at 3000 rpm and decanted. The supernatant from the (-IP) sample (-IP$_{sup}$) was set aside. The beads were then washed and decanted four times with yeast lysis buffer (50 mM HEPES pH 7.6, 1 mM EDTA, 1% Triton X-100, 0.1% sodium deoxycholate, 140 mM NaCl), with the third wash being with a high salt yeast lysis buffer (500 mM NaCl). The beads were then heat eluted for 5 minutes at 95° C. into 100

µL of TE buffer. The supernatant was set aside and heat elution was repeated to give a total volume of 200 µL of supernatant per sample. The supernatants were then extracted by phenol:chloroform:isoamyl alcohol and the top aqueous phase kept in order to remove proteins. A second chloroform extraction was performed to remove as much phenol as possible from the upper aqueous phase. The samples were then tested by LC-MS to confirm the selective immunoprecipitation of TFV by the anti-TFV polyclonal antibody.

Competitive Dot Blot Assay

Nitrocellulose strips were cut to dimensions of approximately 7 mm by 25 mm. BSA-TFV solution in PBS was diluted down to either 1 µg/mL or 100 ng/mL representing about a 1000-fold or 10,000-fold dilution factor. The strips were then spotted 3 times with 1uL of diluted BSA-TFV and allowed to dry. The strips were blocked with 5% milk in tris-buffered saline with Tween 20 (TBS-T) for 30 minutes and washed three times with TBS-T. Samples of TFV were prepared at varying concentrations between 1 ng/mL and 1 µg/mL in either TBS-T or human urine alongside a no TFV control sample. Anti-TFV polyclonal antibody from raw serum (e.g., unpurified) was added to the TFV samples at a dilution of 1:50,000 and incubated at room temperature while rotating for at least 1 hour. The strips were incubated in the spiked urine or TBS-T solutions of TFV and anti-TFV polyclonal antibody at room temperature while rotating for 1 hour and washed three times with TBS-T followed by a high-salt (500 mM NaCl) TBS-T wash and a low-salt (50 mM NaCl) TBS-T wash. The strips were then incubated in a 1:8000 dilution in TBS-T of anti-Rabbit antibody conjugated to HRP at room temperature while rotating for 1 hour and washed three times with TBS-T. The HRP was then visualized by pico chemiluminescent substrate and chemiluminescent photographs were taken by a VersaDoc Imaging Model 4000 system from BioRad.

Antibody Purification

After the development of the dot blot assay, BSA-TFV protein was immobilized onto agarose beads using the CarboxyLink Coupling Gel protocol from ThermoFisher. In short, 2 mL of gel slurry was packed into a disposable column and allowed to settle for 30 minutes. The column was washed with 10 mL of 2-(N-morpholino)ethanesulfonic acid (MES) buffer. 1 mL of approximate 1 mg/mL BSA-TFV solution was desalted into MES buffer using a desalting column and added to the column along with 30 mg EDC dissolved in 0.5 mL MES buffer. The column was capped and the slurry was mixed end-over-end for 3 hours. The column was allowed to drain and washed with 1 mL of 1M NaCl. The presence of protein in the flow-through was tested by Bradford assay against a BSA-TFV control sample to confirm protein remained on the beads. The column was washed with 5-10 mL of 1M NaCl then equilibrated with 6 mL PBS. 5004, of serum was added to the column which was then capped and allowed to incubate for 1 hour at room temperature. The column was then washed with 12 mL of PBS and eluted with 8 mL of 100 mM glycine buffer pH 3.0. Fractions were collected and immediately neutralized by addition of 1004, 1M Tris pH 7.5 buffer. Flow-through, wash, and elution fractions were checked for protein by Bradford assay. Elution fractions containing antibody were pooled and desalted into PBS buffer using a desalting column. The presence of purified antibody was checked by acrylamide gel electrophoresis and functionality of the antibody was checked by immunoprecipitation.

Gold Nanoparticle Conjugation

Conjugation of purified antibody onto gold nanoparticles was performed using an InnovaCoat Gold Conjugation Kit from Innova Biosciences. Briefly, purified antibody was diluted to 0.1 mg/mL in the provided diluent solution. 12 µL of diluted antibody were mixed with 42 µL of the provided reaction buffer. 45 µL of this mixture was then added to a tube of lyophilized 40 nm gold nanoparticles provided by the kit. The nanoparticles were incubated on a rotator at room temperature for 15 minutes. 5 µL of the provided quencher solution was added and the nanoparticles were incubated for an additional 5 minutes. 500 µL of 10× diluted quencher solution in water was added and the nanoparticles were spun down at 9000 g for 10 minutes and decanted. The nanoparticles were suspended in 50 µL of 10× diluted quencher solution and stored at 4° C.

Competitive Lateral Flow Assay

Hi-Flow Plus HF180 nitrocellulose sheets were laser cut into lateral flow strips and chromatography paper was adhered to the end of the strips as a waste reservoir using autoclave tape. Samples of TFV were prepared at varying concentrations between 10 ng/mL and 100 µg/mL in urine alongside a no TFV control sample. For each sample, 1 µL of conjugated gold nanoparticles was added to 244, of PBS and 804, of sample was added. The mixture was allowed to incubate at room temperature on a rotator for at least 30 minutes. 0.3 µL of anti-rabbit antibody was spotted on the strips as a control spot. 0.3 µL of 2.5 µg/mL BSA-TFV was spotted as the test spot on the strips upstream of the control spot. The spots were allowed to dry and another 0.3 µL of BSA-TFV was spotted on top of the test spot. After incubation, concentrated TBS-T was added to each sample such that the final Tween 20 concentration was 0.05%. One end of each of the lateral flow strips was dipped vertically into the sample tubes such that the solution ran up the nitrocellulose strip and into the waste reservoir via capillary action. The strips were incubated in the solution for 25-30 minutes before being photographed with a Nikon DS-Ri2 camera and analyzed via ImageJ.

Lateral Flow Assay Specificity Test

The protocol is the same as the competitive lateral flow assay. Solutions of TFV, AZT, Abcavir, AMP, and adenine were made at concentrations of 100 µg/mL alongside a urine only control sample.

Statistical Analysis of Sensitivity Test

There was a statistically significant difference between groups as determined by one-way ANOVA ($F(5,24)=15.0$, $p=1.02\times10^{-6}$). Tukey's honestly significant difference post hoc test was then performed to identify which concentration groups are significantly different from the no-TFV control. It was found that for 1 µg/mL, 10 µg/mL, and 100 µg/mL TFV concentrations there are statistically significant differences from the no-TFV control.

Results

Generation of Rabbit Anti-TFV Polyclonal Antibody

Figure 2A:
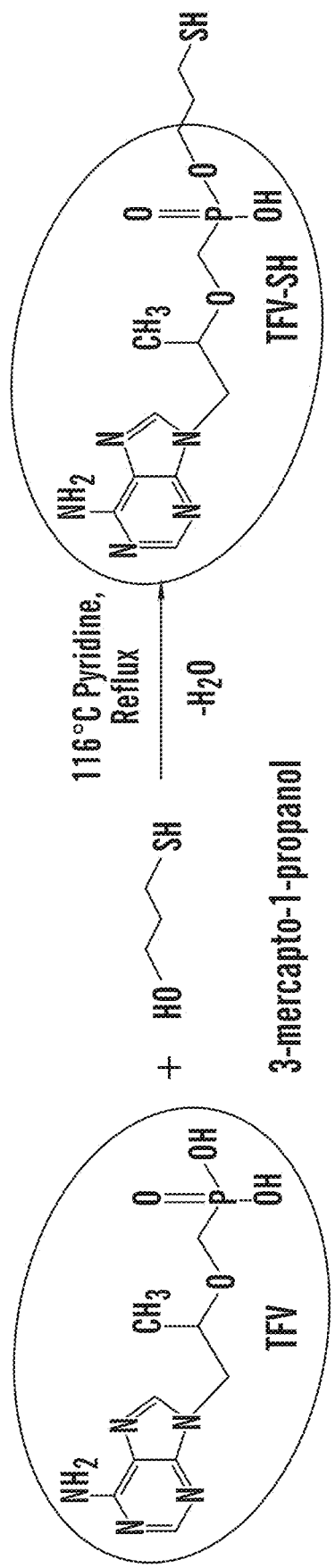
FIG. 2A is a synthesis scheme for the synthesis of thiolated TFV (TFV-SH).

To raise an antibody against TFV the small molecule first was attached to an immunogenic protein prior to rabbit immunization. TFV was modified to contain a reactive thiol side group for conjugation. The thiol group was attached to the phosphonate group of TFV utilizing a synthetic pathway that is similar to how TFV is converted to TDF (Varal, D.; Joshi, M.; Panmand, D.; Jadhav, V. Der Pharma Chem. 2016, 8 (1), 338-343; Hostetler, K. Y.; Kini, G. D.; Beadle, J. R. Phosphonate ester antiviral compounds, 2014). One of the steps in converting TFV into TDF involves reacting TFV with alcohols to add more water-soluble side groups onto the TFV phosphonate. Here we reacted TFV with mercaptoalcohols in order to produce thiol-modified TFV molecules (TFV-SH) as shown in FIG. 2A.

Figure 3A:
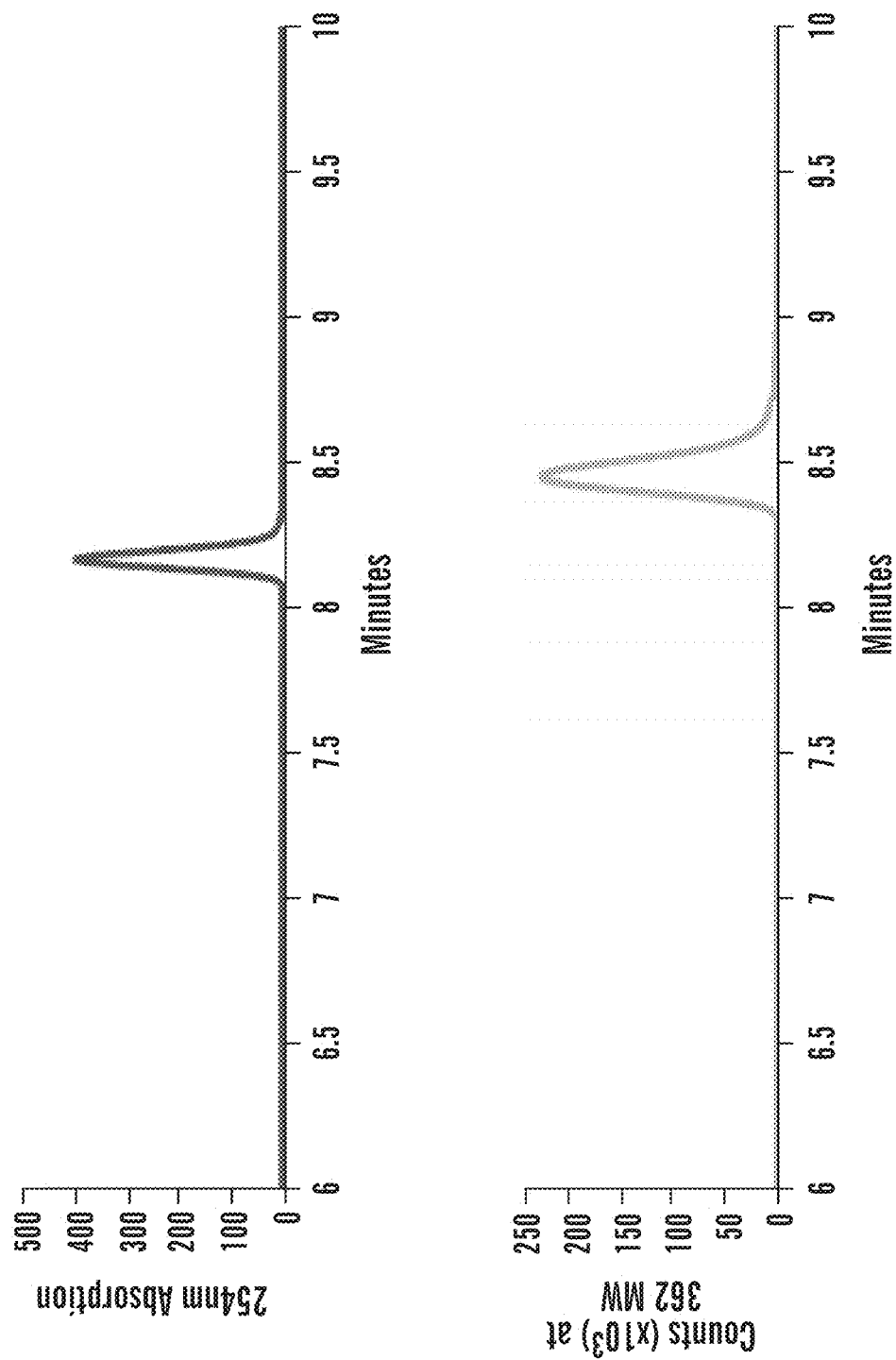
FIG. 3A shows the plot of an LC-MS characterization of purified TFV-SH synthesis product.

After reacting TFV (287MW) with 3-mercapto-1-propanol (92MW) the LC-MS data as shown in FIG. 3A confirms the presence of TFV-SH. The top graph shows data plotted from UV Absorbance at 254 nm data. The bottom graph shows data plotted from the Mass Spec signal of 362 MW data. The synchronized increase in the UV absorbance at 254 nm and the spike in counts by the mass spectrometer of 362MW species at 8.4 minutes demonstrated the existence of TFV-SH. The combination of TFV and 3-mercapto-1-propanol was expected to generate a mass spec signal at 362MW since attachment to the phosphonate side group was expected to liberate a water molecule.

Figure 2B:
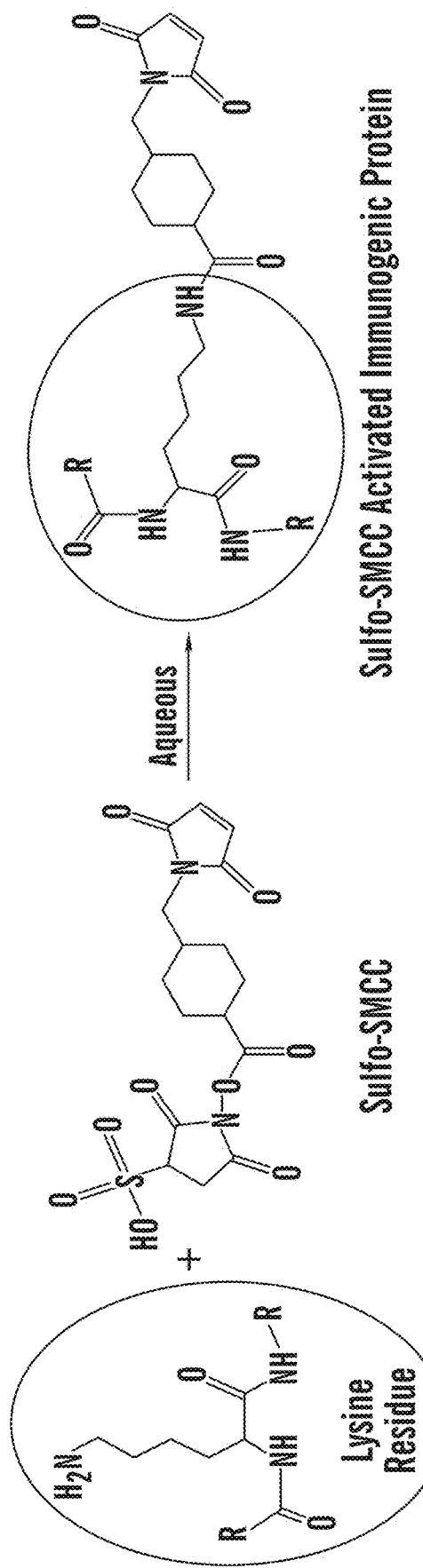
FIG. 2B is a synthesis scheme for conjugation of sulfo-succinimidyl 4-(N-maleimidomethyl)cyclohexane-1-carboxylate (sulfo-SMCC) to the lysine residue of a protein.
Figure 2C:
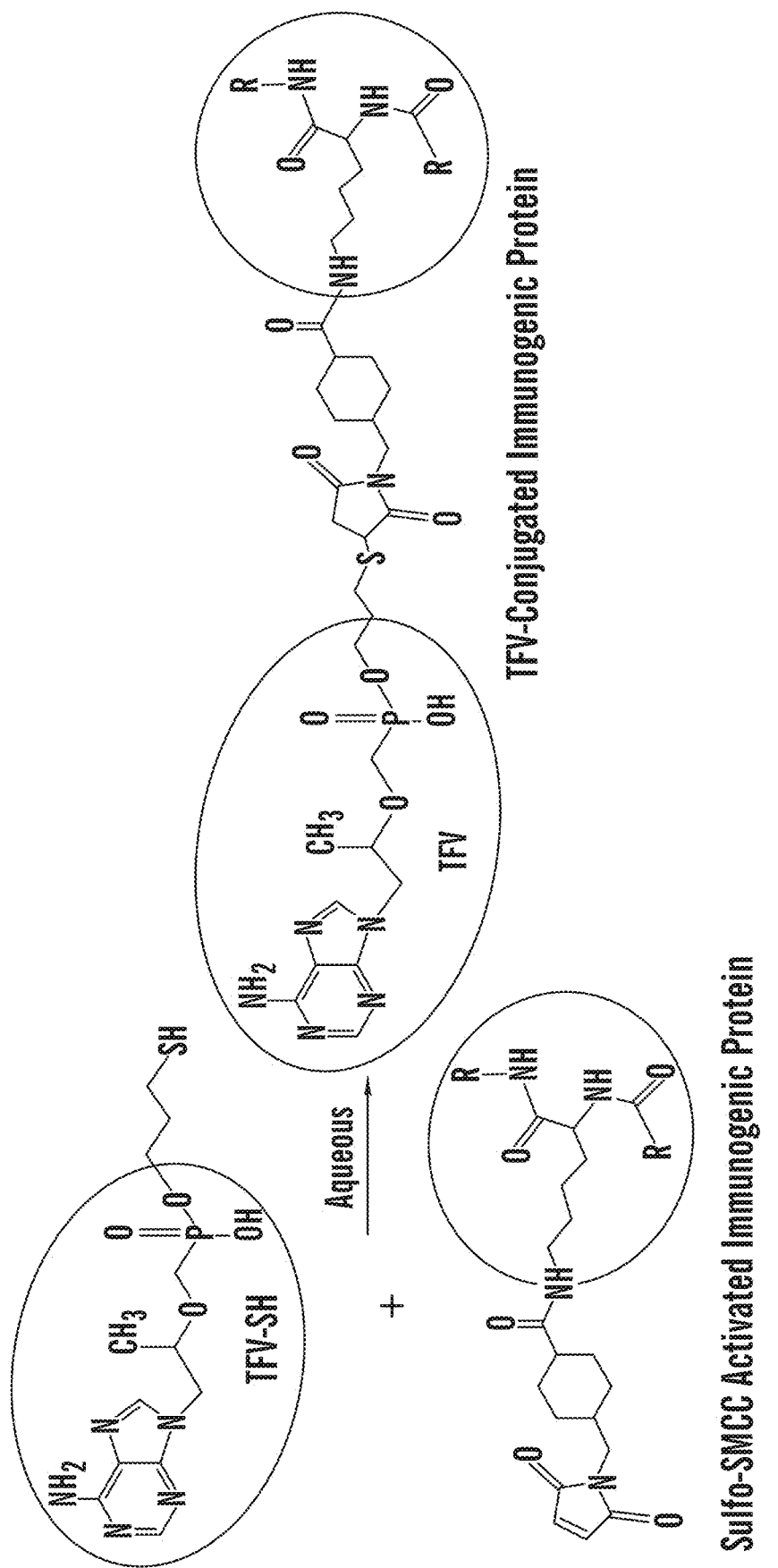
FIG. 2C is a synthesis scheme for preparing a TFV-conjugated immunogenic protein.

Once TFV-SH was synthesized the molecule was attached to KLH and to BSA by adding a maleimide side group to each of the proteins as outlined in FIG. 2B and then conjugating the thiol group of the TFV-SH to the maleimide as shown in FIG. 2C. The increase in molecular weight of the BSA molecule is demonstrated by MALDI and shown in FIG. 3B, confirmed the successful conjugation of TFV-SH to the proteins. BSA has a MW of 66,463. The purified KLH-TFV conjugate was then injected into rabbits to generate polyclonal antibodies against TFV.

Figure 4:
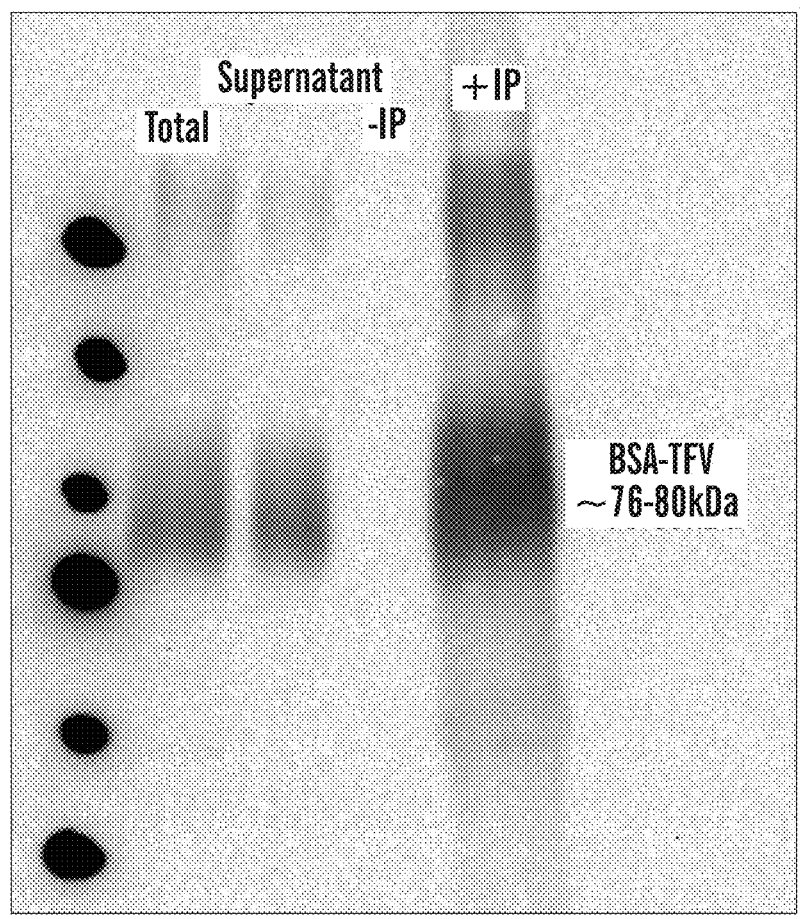
FIG. 4 shows immunoprecipitation of BSA-TFV by anti-TFV polyclonal antibody.

Serum from KLH-TFV immunized rabbits was analyzed to confirm the presence of TFV-sensitive antibodies. First, traditional western blotting and immunoprecipitation experiments were conducted to confirm the specific and sensitive antibody binding of the polyclonal antibody to BSA-TFV conjugates (FIG. 4). While these successful tests, especially the successful immunoprecipitation of BSA-TFV in the presence of BSA and whole cell lysate, were highly suggestive of the presence of TFV-binding polyclonal antibodies they did not demonstrate direct binding of the antibody to native, unmodified TFV. However, since TFV is a small molecule neither western blotting nor traditional immunoprecipitation experiments would be appropriate. As such, a modified immunoprecipitation protocol as described above was performed. In short, rather than transferring the immunoprecipitated sample to a gel for western blotting the proteins were removed from the sample via phenol:chloroform:isoamyl alcohol purification and the resulting solution was analyzed using LC-MS. The confirmed presence of TFV in this sample as shown in FIG. 3C, demonstrated the successful generation of TFV-sensitive polyclonal antibodies. The corresponding absence of AMP, which is a nucleotide analogue of TFV and was present at a 20× higher concentration than TFV in the initial immunoprecipitation sample (FIG. 3C inset), established the high specificity the antibody has to TFV.

After the initial validation of the anti-TFV antibody a nitrocellulose-based dot blot assay was performed to detect the presence of TFV in spiked urine samples. Spiked urine samples with varying amounts of TFV were incubated with the anti-TFV antibody and nitrocellulose strips were spotted with BSA-TFV. Since it had been established that the anti-TFV antibody is sensitive to both molecules it was considered relevant to show that after incubation with TFV that the antibody would be "blocked" and unable to bind BSA-TFV immobilized on the surface. The results of the dot blot assay are shown in FIG. 5 which demonstrates the validity of deploying a competitive assay for the detection of TFV. FIG. 5 Panel i demonstrates protein spotting by BSA-TFV on nitrocellulose strips. FIG. 5 Panel ii shows competitive dot blot assay performed on BSA-TFV spotted nitrocellulose strips. A decrease in signal (decrease in brightness of the spot in the figure) corresponds to an increase in TFV urinary concentration. The assay has a lower limit of detection of 35 nM in urine (about 10 ng/mL) using an HRP-coupled secondary antibody. Additionally, the success of the assay in a complex solution such as urine further supports good specificity of the antibody to TFV. The successful detection of TFV in spiked urine samples using a competitive dot blot assay suggested that the anti-TFV antibody is suitable for use in a lateral flow device.

Detection of TFV by a Gold Nanoparticle Lateral Flow Strip

Translation of the dot blot assay into a lateral flow configuration required immobilization of the anti-TFV antibody to gold nanoparticles. First, the serum was processed using affinity purification to isolate antibodies that bound BSA-TFV and was validated by immunoprecipitation (FIG. 6) to confirm that the purified antibody was still functional. The antibody was then conjugated to 40 nm gold nanoparticles for use in the lateral flow assay.

The lateral flow assay is based on the same principles as the dot blot assay, as described with reference to FIGS. 7A and 7B. In FIG. 7A, a test sample wherein TFV and added Anti-TFV conjugated to Au nanoparticles are present is labeled as 1. The movement of the anti-TFV gold nanoparticles saturated with TFV across a lateral flow assay is shown as 2. The detection region of the lateral flow strip where saturated anti-TFV gold nanoparticles attach to anti-Rabbit, not binding to BSA-TFV is shown as 3. FIG. 7B, illustrates that as the amount of TFV increases in the sample the test spot intensity decreases (where −TFV spot is shown to the left and +TFV is shown to the right). The control spot having anti-Rabbit remains visible for −TFV and +TFV.

Anti-TFV antibody conjugated to gold beads was incubated with TFV-spiked urine samples and allowed to flow over a nitrocellulose strip containing spotted BSA-TFV followed by anti-rabbit antibody spotted downstream. FIG. 7C is an image showing the sensitivity of a test of competitive gold nanoparticle lateral flow assay in TFV-spiked urine samples. The concentrations of TFV are 0 (control), 10 ng/mL, 100 ng/mL, 1 μg/mL, 10 μg/mL and 100 μg/mL. The intensity of the test spot decreases as the amount of TFV spiked in the sample increases while the control anti-Rabbit test spot remains approximately the same. FIG. 7D shows a plot of quantified data from the competitive gold nanoparticle lateral flow assay. Strips were imaged and processed by ImageJ to get background-normalized intensity measurements of test spots for varying concentrations of TFV spiked into urine. Points with asterisks are statistically significant compared to the no-TFV control strips (N=5). FIG. 8 shows results of a specificity test, where a where the top spot is the control spot, the lower spot is the test spot (100 μg/mL). From left to right the test shows control, TFV, Abcavir, AMP, AZT and Adenine. The test area shows no staining for TFV sample (positive for TFV) while the control area is stained while all other tests show staining in both the test area and control area. The results of the assay shown in FIG. 7C, FIG. 7D and FIG. 8 show a sensitive, statistically significant, and specific detection of TFV in spiked urine samples with a preliminary lower limit of detection of 1 μg/mL.

Discussion

Raising and deploying an antibody against a small molecule presents several challenges. Initially the desired antigen is often not large enough on its own to generate the immune response necessary in the host for antibody development. As a result, the desired antigen, referred to as a hapten, must be conjugated onto a carrier protein to coax an immune response from the host (Murphy, K. In Janeway's Immunobiology. 8th edn.; Lawrence, E., Ed.; Garland Science: New York, 2012; pp 718-719; Karu, A. E.; Goodrow, M. H.; Schmidt, D. J.; Hammock, B. D.; Bigelow1 1, M. W. J. Agric. Food Chem 1994, 42, 301-309(28); Weltzien, H. U.; Moulon, C.; Martin, S.; Padovan, E.; Hartmann, U.; Kohler, J. Toxicology 1996, 107, 141-151; Ertekin, 0.; Ozturk, S.; Ozturk, Z. Z. Sensors (Switzerland) 2016, 16 (8), 1-12).

Another challenge in the development of small molecule-sensitive antibodies is characterization of the host serum after immunization. For protein targets gel electrophoresis is a common technique to isolate and visualize antibody-protein interactions. However, since small molecules are not characterized by gel electrophoresis other techniques such as quartz crystal microbalance must be used to confirm antibody-target binding (Ertekin, O.; Ozturk, S.; Ozturk, Z. Z. Sensors (Switzerland) 2016, 16 (8), 1-12), surface plasmon resonance (Wittenberg, N. J.; Wootla, B.; Jordan, L. R.; Denic, A.; Warrington, A. E.; Oh, S.-H.; Rodriguez, M. Expert Rev. Neurother. 2014, 14 (4), 449-463), and mass spectrometry (Kumar, V.; Barnidge, D. R.; Chen, L.-S.; Twentyman, J. M.; Cradic, K. W.; Grebe, S. K.; Singh, R. J. Clin. Chem. 2010, 56 (2), 306-313).

Additionally, small molecule targets present a difficult challenge to some deployment methods in lateral flow setups. One lateral flow configuration uses antibodies in a sandwich assay to both capture and visualize the same molecule using two antibodies, one immobilized to the lateral flow substrate and the other linked to a visualization moiety. This method relies on large targets such as peptides and proteins that have multiple antibody-binding sites to allow both antibodies to bind. Some small molecules, however, often only have a single antibody-binding site and in these instances the sandwich assay cannot be used. For small molecules competitive ELISAs are often used (Afshar, A.; Thomas, F. C.; Wright, P. F.; Shapiro, J. L.; Anderson, J. Vet. Rec. 1989, 124 (6), 136-141; Perrett, L. L.; McGiven, J. A.; Brew, S. D.; Stack, J. A. Croat. Med. J. 2010, 51 (4), 314-319; Cheng, S.; Shi, F.; Jiang, X.; Wang, L.; Chen, W.; Zhu, C. Anal. Chem. 2012, 84 (5), 2129-2132). Many of these difficulties are overcome by the methods disclosed herein.

Figure 3B:
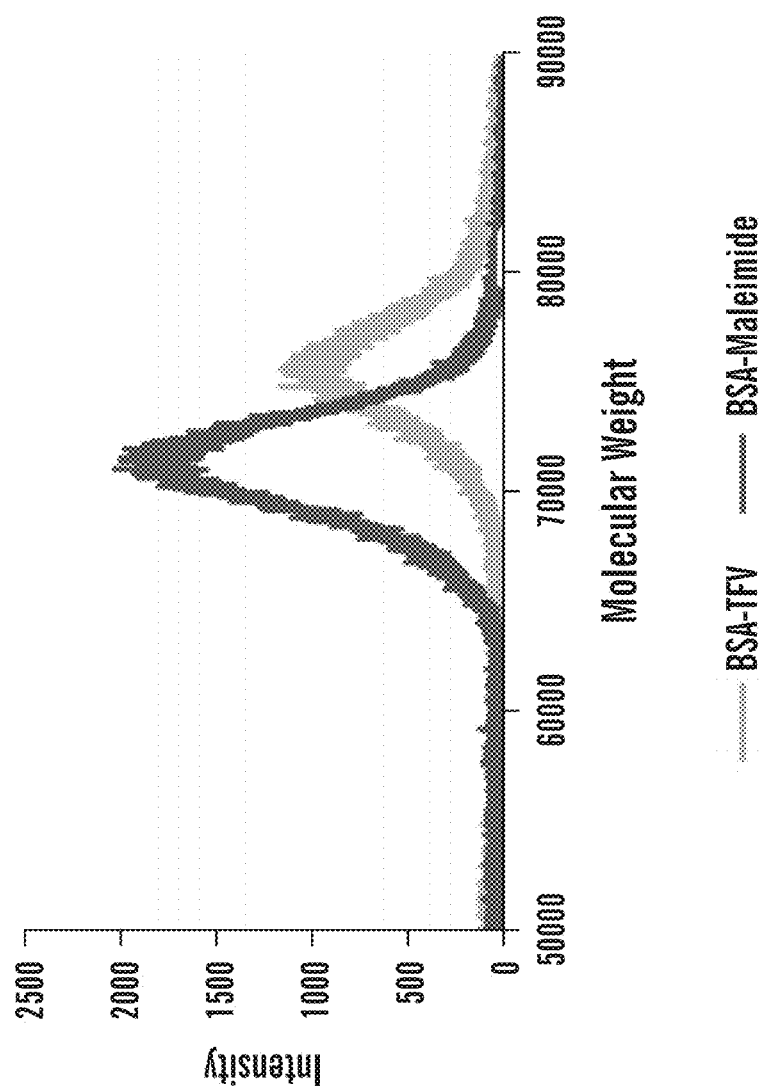
FIG. 3B shows MALDI measurement plots of a BSA-Maleimide intermediate and a BSA-TFV conjugate.
Figure 3C:
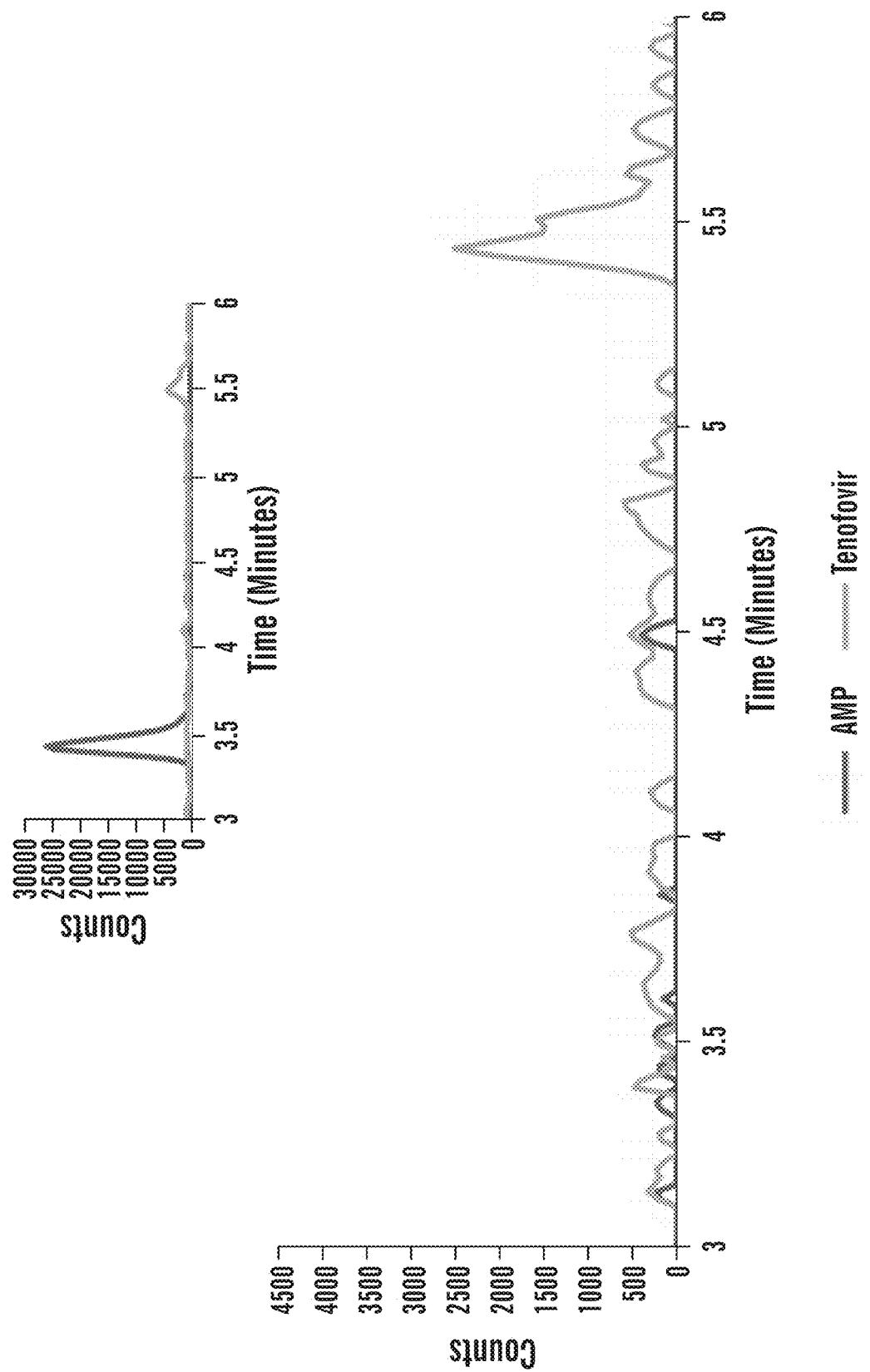
FIG. 3C Shows an LC-MS characterization plot of a TFV immunoprecipitation product and (inset) a plot of pre-immunoprecipitation sample.

Attaching TFV onto a carrier protein required modification of the molecule because the molecule is not easily directly conjugated. A thiol was attached to the TFV molecule to enable the use of Sulfo-SMCC to link thiol-containing molecules to proteins (Calcagno, A.; Cusato, J.; Marinaro, L.; Trentini, L.; Alcantarini, C.; Mussa, M.; Simiele, M.; D'Avolio, A.; Di Perri, G.; Bonora, S. Pharmacogenomics J. 2016, 16 (6), 514-518). FIG. 3B demonstrates how the two-step reaction first added the Sulfo-SMCC to BSA through the reaction of primary amines (from lysine residues) with NHS on the Sulfo-SMCC then added the TFV-SH molecule through the reaction of the thiol group to the maleimide of the Sulfo-SMCC. It is noted that the MALDI data presented in FIG. 3B shows the results of TFV conjugation onto BSA, not the results of conjugation onto KLH. KLH is too large of a protein (390 kDa) for convenient MALDI measurements and therefore BSA-TFV was measured and it is understood that the KLH-TFV reaction proceeded with similar efficiency.

Figure 6:
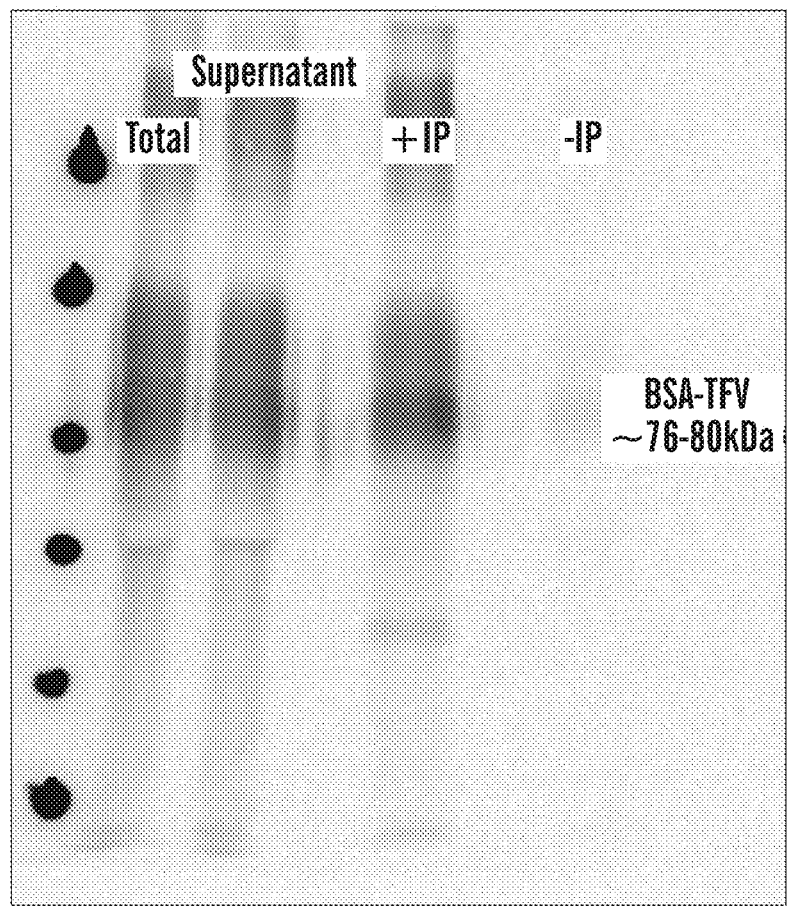
FIG. 6 shows immunoprecipitation of BSA-TFV by affinity column purified anti-TFV polyclonal antibody.
Figure 7A:
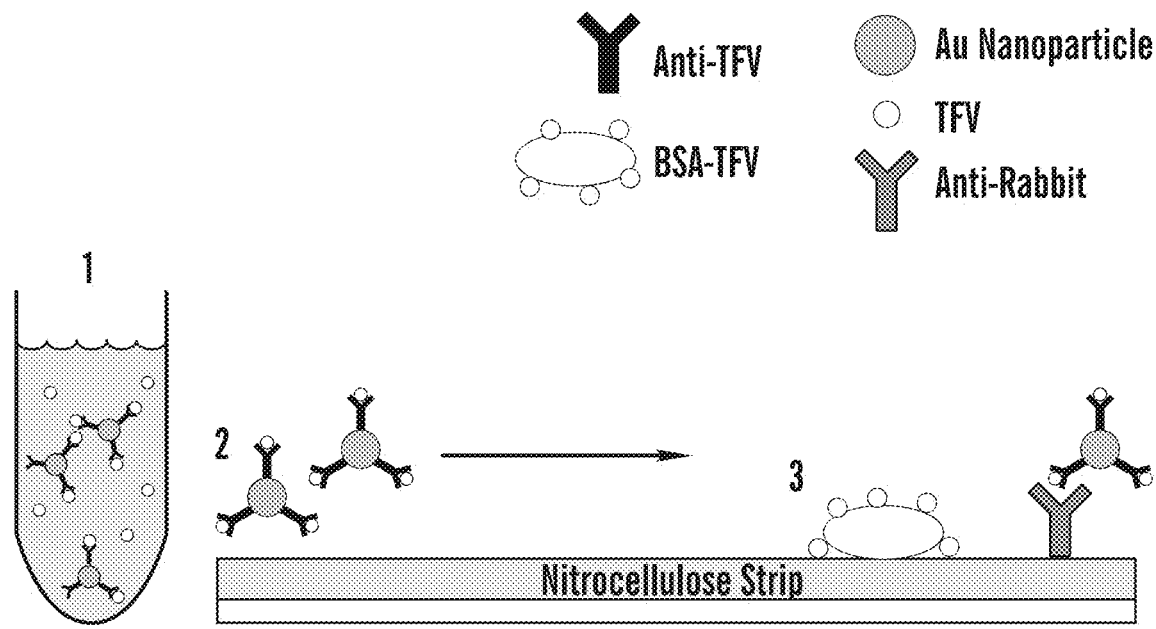
FIG. 7A is a schematic representation showing a competitive gold nanoparticle lateral flow assay.
Figure 7B:
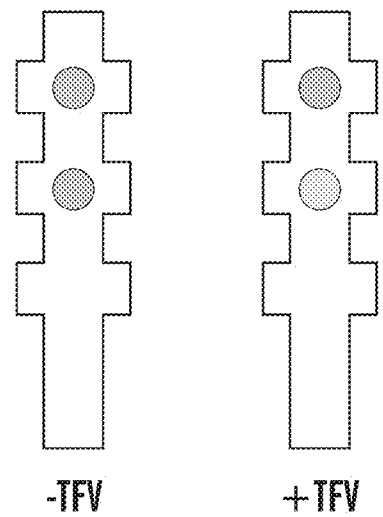
FIG. 7B shows diagrammatically a test strip indicating the expected output of competitive gold nanoparticle lateral flow assay with a –TFV (left) and +TFV (right).
Figure 7C:
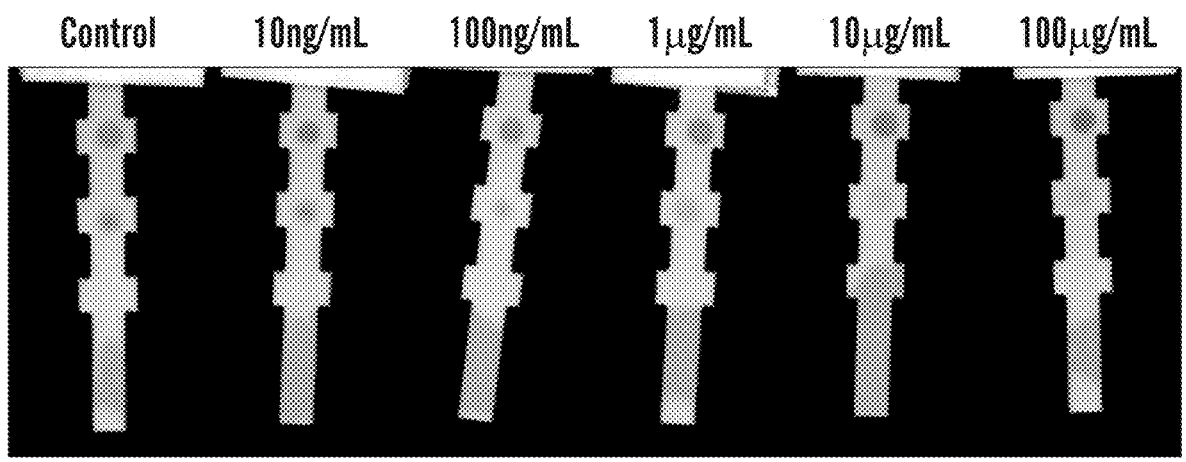
FIG. 7C is an image showing the sensitivity of a test of competitive gold nanoparticle lateral flow assay in TFV-spiked urine samples.
Figure 7D:
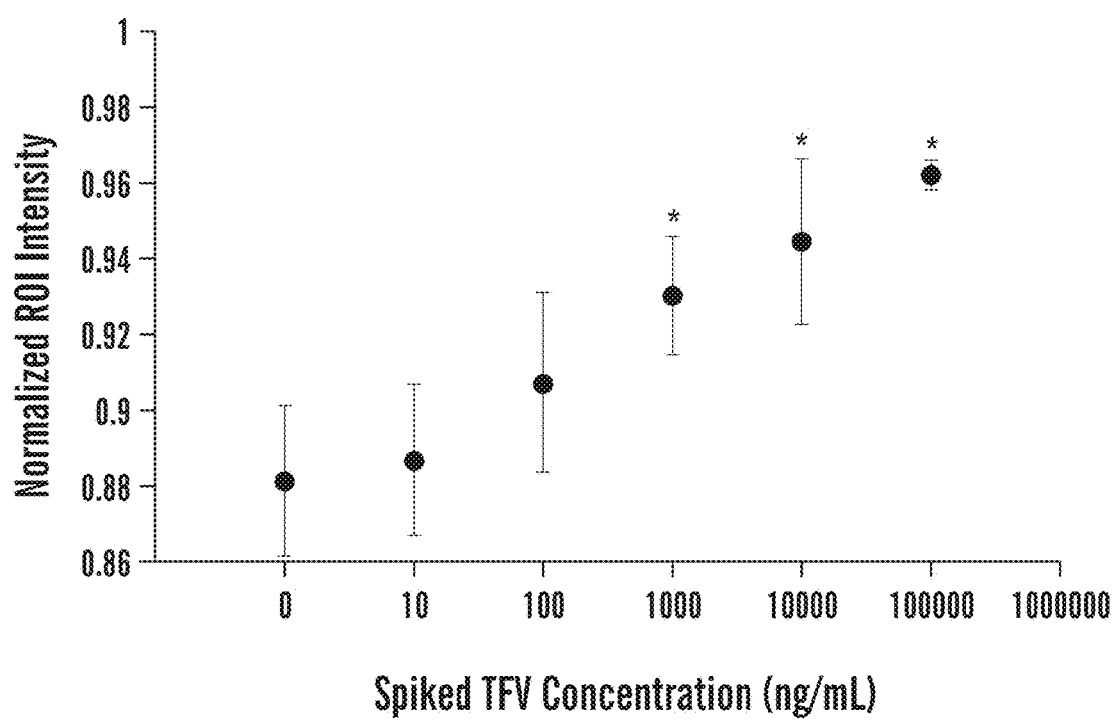
FIG. 7D shows a plot of quantified data from the competitive gold nanoparticle lateral flow assay.
Figure 8:
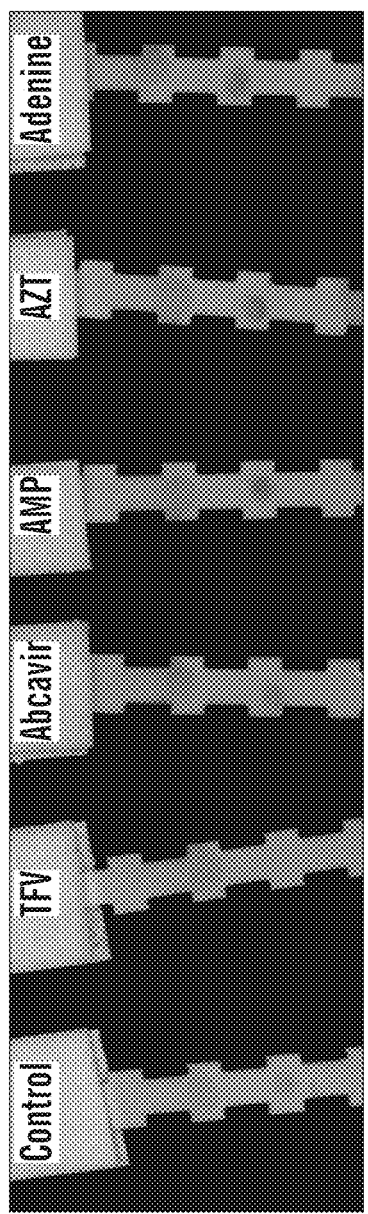
FIG. 8 is an image showing the specificity of a test of competitive gold nanoparticle in a lateral flow assay for TFV.

After immunization the serum was analyzed to confirm that the polyclonal antibody generated was both sensitive and specific to TFV. FIGS. 4 and 6 show that the anti-TFV antibody is sensitive and specific to BSA-TFV and TFV, respectively. The immunoprecipitations were done in the presence of excess whole cell lysate or AMP to demonstrate the specificity of the antibody. AMP was chosen because of the structural similarities to TFV and because adenosine in general can be present in urine. Since TFV samples cannot be characterized by standard western blotting the Protein G beads were eluted and the sample purified using phenol: chloroform:isoamyl alcohol mixture before LC-MS measurements were taken to demonstrate the sensitivity and specificity of the antibody to TFV.

Using the anti-TFV antibody obtained as described above, a competitive assay to detect TFV was developed. As in other competitive ELISAs, the principle of the assay is that as the concentration of TFV in the sample increases and more of the anti-TFV antibody is bound to free floating TFV, less of the anti-TFV antibody is unbound and available to bind to the BSA-TFV immobilized onto a nitrocellulose substrate. The result is that when incubated in anti-rabbit HRP secondary antibody the chemiluminescent signal of these spots is indirectly proportional to the amount of free TFV in the original sample.

Figure 9:
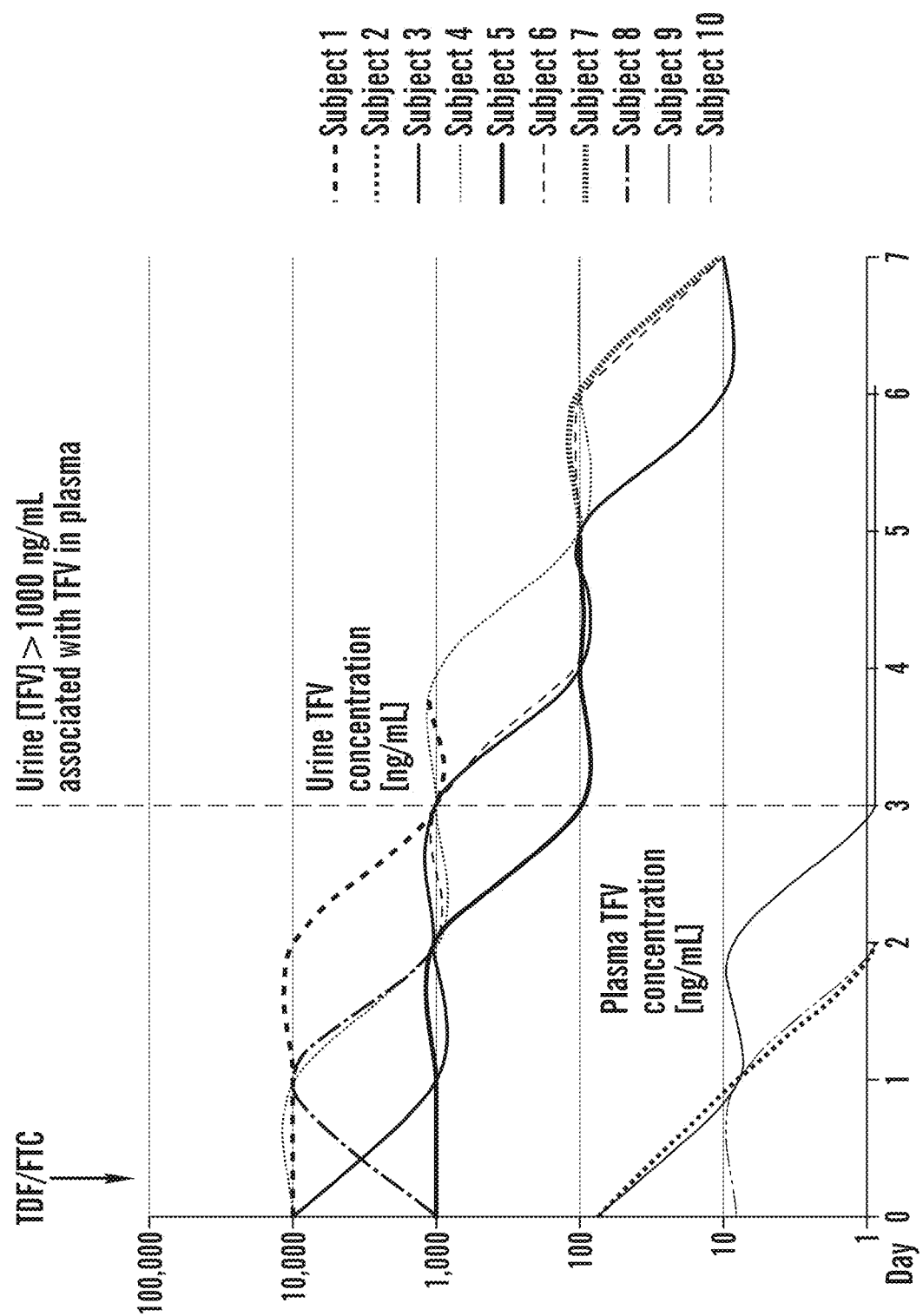
FIG. 9 shows a plot of the change in concentration of TFV over time for samples from ten subjects.

TFV-spiked urine was used as a model biological sample. Urine provides several advantages in monitoring TFV adherence. Urine tests are non-invasive compared to assays that measure plasma. For patients on TFV regimens the urinary concentration of TFV is usually over 100× more concentrated than the plasma concentration (Koenig, H.; Mounzer, K.; Daughtridge, G.; Sloan, C.; Lalley-Chareczko, L.; Moorthy, G.; Conyngham, S.; Zuppa, A.; Montaner, L.; Tebas, P. HIV Med. 2017). Also, urine does not require any sample preparation before testing in the assay. FIG. 9 Shows urinary excretion over time of TFV after a single dose of TDF/FTC (tenofovir/emtricitabine) for 10 subjects.

Figure 5:
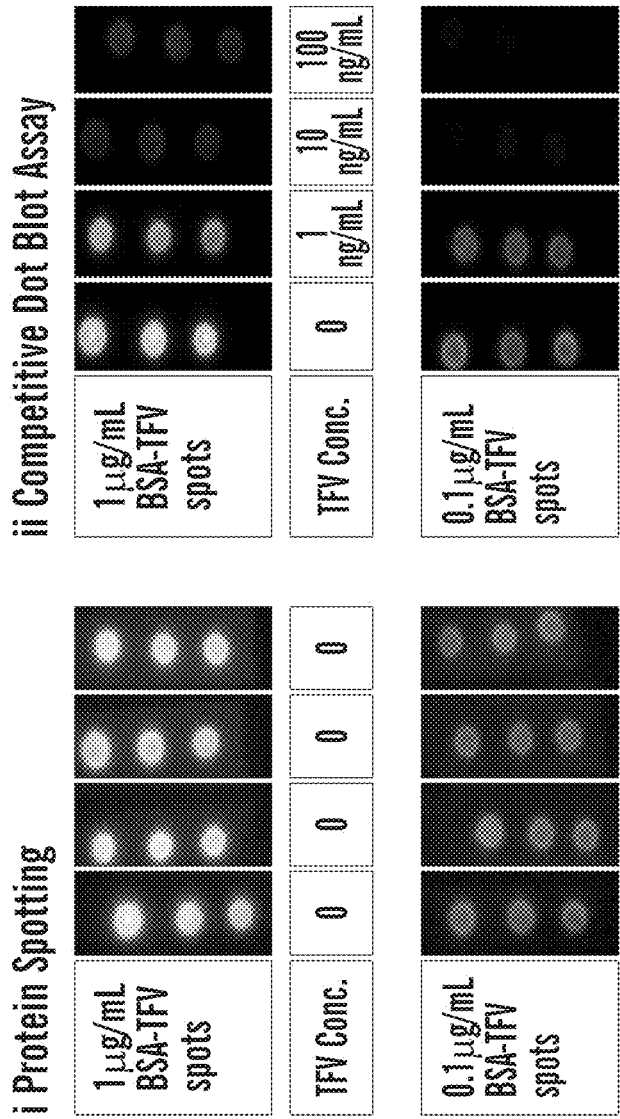
FIG. 5 is an image of a dot blot assay demonstrating a competitive assay for the detection of TFV.

FIG. 5 validates that the competitive assay works with spiked urine samples and that TFV can be detected at concentrations as low as 1ong/mL. It was noted that the BSA-TFV protein spots required dilution of several orders of magnitude before being spotted onto the nitrocellulose strips. When undiluted BSA-TFV (~1 mg/mL) is spotted onto the strips the assay can no longer differentiate between TFV-positive and TFV-negative samples (data not shown). It is not known why spotted protein needs to be diluted down to a concentration as low as 1 µg/mL for the assay to perform as desired, but, without being bound by a specific theory, it is speculated that an overabundance of protein on the nitrocellulose spots can increase non-specific binding of either the anti-TFV or anti-rabbit HRP antibodies resulting in high non-specific signal.

The assay to detect TFV in urine needs to be sensitive enough to identify patients that are properly adhering to their regimens and those who are not. For a patient taking 300 mg TDF daily the urine concentration of TFV is around 23 µg/mL (Calcagno, A.; Cusato, J.; Marinaro, L.; Trentini, L.; Alcantarini, C.; Mussa, M.; Simiele, M.; D'Avolio, A.; Di Perri, G.; Bonora, S. Pharmacogenomics J. 2016, 16 (6), 514-518). When 300 mg of TFV is ingested only once the concentration of TFV in urine after 24-72 hours has been reported to be around 1-10 µg/mL (Koenig, H.; Mounzer, K.; Daughtridge, G.; Sloan, C.; Lalley-Chareczko, L.; Moorthy, G.; Conyngham, S.; Zuppa, A.; Montaner, L.; Tebas, P. HIV Med. 2017). The increased use of TAF as an alternative to TDF in drug regimens will probably shift these sensitivity windows. TAF is dosed at 25 mg per day and thus results in about a 10× decrease in TFV plasma concentrations (Ray, A. S.; Fordyce, M. W.; Hitchcock, M. J. M. Antiviral Res. 2016, 125, 63-70). Assuming this also leads to a 10× decrease in TFV urine concentrations, it would suggest that daily doses of 25 mg TAF would result in about 2.3 µg/mL of TFV in urine as a gross estimate. The 24-72 hour TFV urine concentration after a single 25 mg dose of TAF would similarly be estimated to be around 0.1-1 µg/mL.

All of these pertinent concentration windows are detectable using the competitive dot blot assay which has a sensitivity as low as 10 ng/mL. It is relevant, however, to consider that long/mL can be too sensitive for practical use. According to recent work by Koenig et al., an isolated TFV dose would result in urinary TFV concentrations above long/mL for the next week (Koenig, H.; Mounzer, K.; Daughtridge, G.; Sloan, C.; Lalley-Chareczko, L.; Moorthy, G.; Conyngham, S.; Zuppa, A.; Montaner, L.; Tebas, P. HIV Med. 2017). A strength of this assay is that the effective sensitivity can be tuned by changing the amount of anti-TFV antibody that is incubated with a sample. Increasing the amount of antibody that is incubated with the sample would increase the amount of TFV required to prevent antibody binding to the spotted BSA-TFV, thus allowing the assay sensitivity to be tuned to selectively detect desired concentration windows. For a sensitivity of 10 ng/mL the dot blot assay required a 50,000× dilution factor of the raw serum into the sample. Theoretically, a 500× or 50× dilution factor of the serum into the sample would result in a sensitivity limit between 1 μg/mL and 10 μg/mL.

While the dot blot assay is a flexible and sensitive assay and one embodiment of the invention, there are limitations that hinder potential deployment in the clinic especially in resource-limited settings where the need is greatest. The dot blot assay protocol requires many steps including nitrocellulose blocking and membrane incubations that increase the time required (at least 3 hours) to get a result. Also, chemiluminescent measurements generally require some capital investment by the clinic in equipment and training to get visual results. To address these concerns, and to develop an assay that is more suitable for deployment, a gold nanoparticle lateral flow strip assay was designed for faster and more affordable TFV adherence monitoring. The flow assay is another embodiment of the invention.

The gold nanoparticle lateral flow strip assay generates a clear colorimetric readout requiring less time, training, and equipment than the HRP-based dot blot assay. As higher concentrations of TFV samples are assayed the signal strength of the BSA-TFV test spot decreases as the anti-rabbit antibody control spot remains relatively constant. The sensitivity down to 1 ug/mL and the high specificity of the anti-TFV antibody suggests the lateral flow assay can be used for assaying urine samples of HIV patients prescribed TFV-containing drug regimens. The speed and simplicity of the lateral flow assay is an improvement over the HRP-based assay for potential deployment in resource-limited settings.

Test for Isoniazid

Isoniazid (INH) is metabolized into isonicotinic acid (INA) in vivo, and can be colorimetrically detected via by a multistep reaction known as the Arkansas Test. The test requires bulk mixing and pipetting of reagents in which the final barbituric acid component reacts with the previous ones to produce polymethine blue dye upon reaction with isonicotinic acid. A major drawback of the Arkansas Test is the toxicity of potassium cyanide. A modified version of the test that uses potassium thiocyanate, citric acid and barbituric acid dried onto a paper strip following Kilburn's earlier work. The current version is meant for a lab based test use. In one embodiment, the test can be modified into a lateral flow format. In another embodiment, paper strips will be laser cut to encode the test results so they cannot be cheated by a remote tester.

Figure 10:
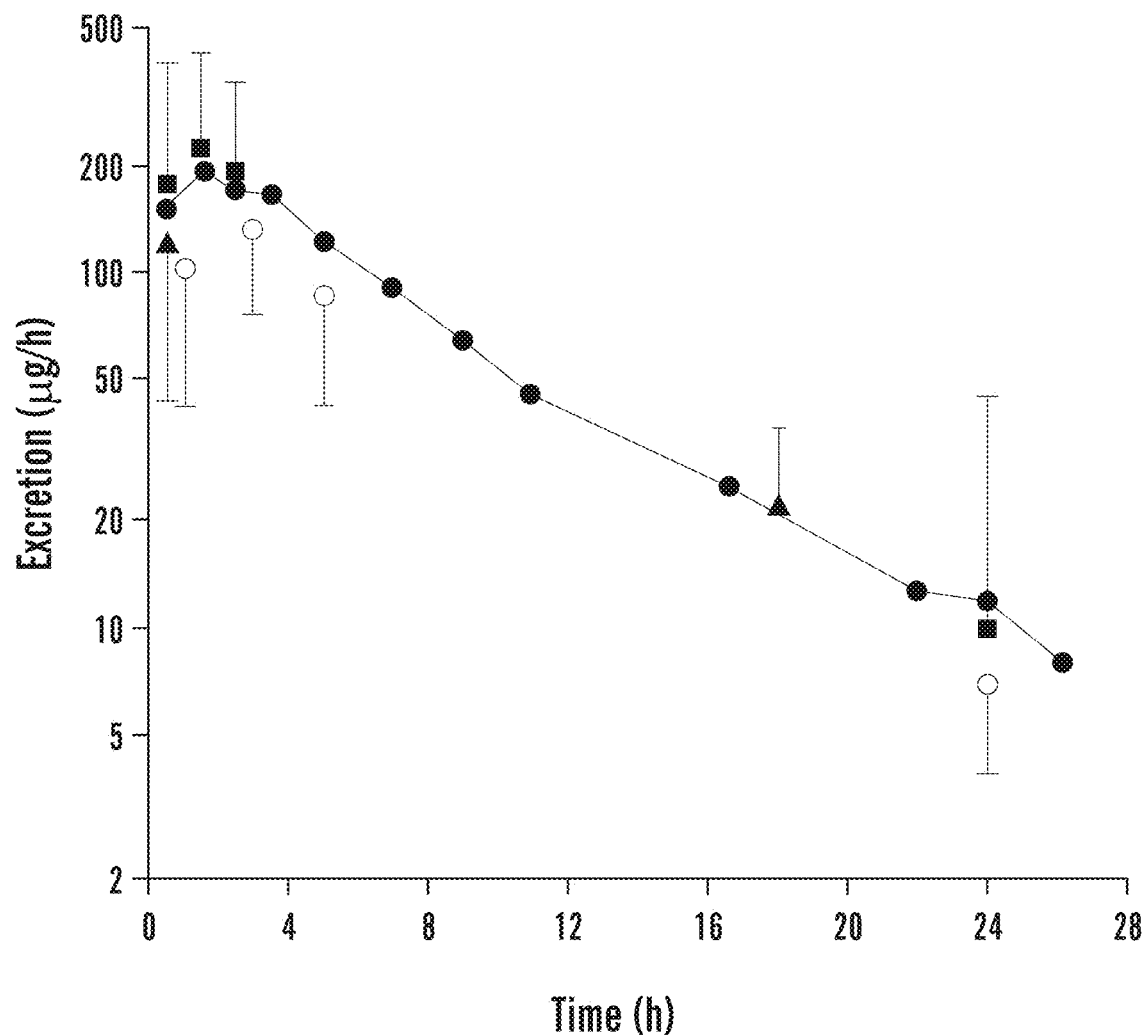
FIG. 10 is a plot showing a qualitative time course for urinary excretion of INA, as measured by a color assay done in test tubes.

Typical doses of INH drugs for a 50 kg patient is 250 mg/day. INH is metabolized to form acetyl-INH and isonicotinic acid (INA); 30-40% of the oral dose is recovered in the urine within 24 hr as INA giving urinary concentrations of the order 100 μg/ml. FIG. 10 shows a qualitative time course for urinary excretion of INA, as measured by a color assay done in test tubes.

Figure 11A:
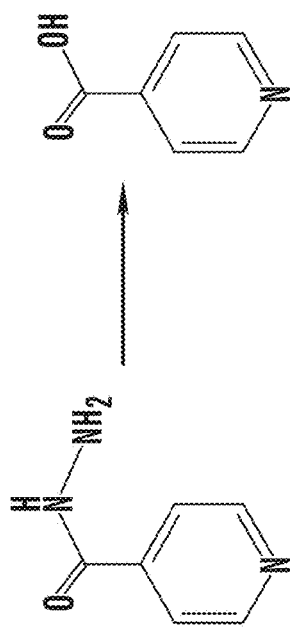
FIG. 11A schematically shows the metabolism of isoniazid (INH) to isonicotinic acid (INA) which occurs in vivo.
Figure 11C:
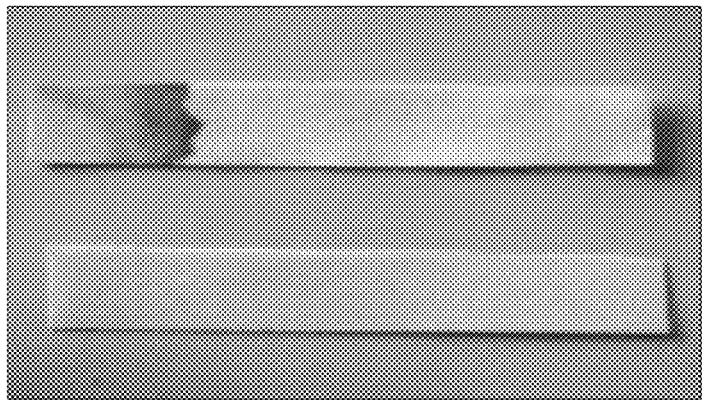
FIG. 11C is an image of INH adherence test strips.
Figure 11B:
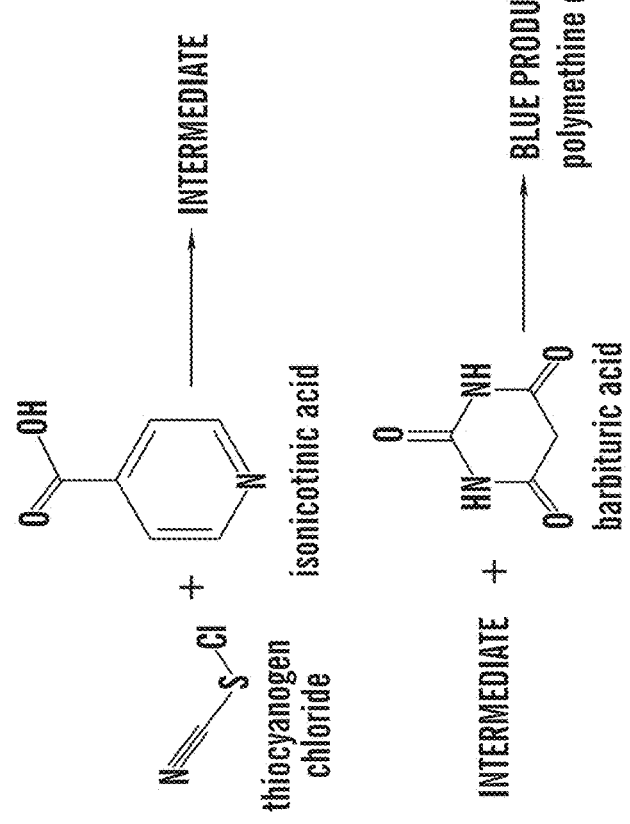
FIG. 11B depicts the chemical reaction steps used for colorimetric determination of INH.

The modified version of this assay is described with reference to FIGS. 11A, 11B and 11C. FIG. 11A schematically shows the metabolism of isoniazid (INH) to isonicotinic acid (INA) which occurs in vivo. FIG. 11B depicts the chemical reaction steps used for colorimetric determination of INH. Thiocyanogen chloride reacts with isonicotinic acid producing an intermediate that when reacted with barbituric acid produces a polymethine dye which has a blue color. In the modified version that can be performed on paper strips, the components are dried on filter paper and separated by length along a continuous strip. This architecture can be modified to prevent premature reaction of the elements due to humidity or mishandling. Solutions of potassium thiocyanate (KSCN), and barbituric acid (pH 4.5) can be prepared by dissolving in water. Reagents can be spotted onto dry filter paper as a substrate. A multistep paper fluidic circuit with 4 mm×4 mm spotted swatches with 20 μL of each solution can be prepared on Whatman #1 chromatography paper. FIG. 11C is an image of a resulting INH adherence test strips. A negative (left stip) shows no coloration. A positive (right strip) shows the blue coloration at the top, detecting portion of the strip.

Combined TFV and INH Urine Dipstick Test

One embodiment of the invention includes a multiplexed test for TFV and INH. The test can be conducted, for example, on a lateral flow strip having both the modified Arkansas Test and the TFV testing capability. For example, where in one device at least two strips are included, one for INH and the other for TFV. Alternatively, the embodiment can include on one strip features (e.g., regents) as herein described for detecting INH and features (e.g., antibodies and drugs) for detecting TFV.

Coded Test Allow Providers to Leverage Incentive Based Adherence Techniques

In some embodiments, the tests are amenable for remote monitoring of patient compliance by using encrypted, diagnostic paper microfluidic strips that detect metabolites of INH and TFV in urine. In this embodiment the paper fluidic platform is engineered to display alphanumeric coded messages instead of just yes/no results, as depicted by the workflow in FIG. 12. Panel i, depicts a device such as a mobile phone to which the patient information system sends a unique button activation code. Panel ii, depicts an image of a lateral flow test output. In this step the patient activates an interactive diagnostic and uses the test. The alphanumeric code is revealed, as depicted in the image of the test, matching positive reaction sites. Panel iii, depicts an image of a device such as the mobile phone which the patient can use to send an SMS message with the alphanumeric code. Panel iv, depicts an image of a device such as the mobile phone wherein the message is sent and captured by the patient information system. Such codes can be encrypted and only revealed in the presence of a user provided metabolite. Moreover, they are dynamically changed by receiving a delayed periodic activation instruction by a clinician using a simple SMS instruction or a phone call. The dual key system ensures that patients cannot game the remote monitoring system by providing premature results. Making the test results coded does not require any new biochemistry and is dependent only on the internal fluidic design of the test. Testing and coded result reporting via telemedicine can be incentivized by a monetary rewards program. These three components—remote diagnostics, mobile telephony, and economic incentives, are significantly less resource-intensive than DOTS, the current standard, which involves on-site, in-person monitoring of compliance. In addition, this platform can permit the aggregation of reliable and accurate compliance data thereby facilitating real-time program evaluation, can enable efficient deployment of resources within a community, and finally, can give providers the means to focus on patients with the greatest risk of non-compliant.

While the present disclosure describes detection of TFV, presence of other drugs and/or metabolites in test samples can also be detected in a similar way. The assay is also flexible enough to be immediately paired up with other low-cost monitoring devices for drug regimens in the treatment of diseases that are commonly co-infected with HIV such as hepatitis (Uneke, C. J.; Ogbu, O.; Inyama, P. U.; Anyanwu, G. I.; Njoku, M. O.; Idoko, J. H. Mem. Inst. Oswaldo Cruz 2005, 100 (1), 13-16; Hoffmann, C. J.; Thio, C. L. Lancet Infect. Dis. 2007, 7 (6), 402-409) and tuberculosis (Tiberi, S.; Carvalho, A. C. C.; Sulis, G.; Vaghela, D.; Rendon, A.; Mello, F. C. de Q.; Rahman, A.; Matin, N.; Zumla, A.; Pontali, E. Presse Med. 2017, 46 (2), e23-e39). Along with multiplexing, increasing the contrast between TFV-negative and TFV-positive assay results can enhance/increase sensitivity. Further, the design can be altered such that the appearance and increased intensity of the test spot indicates a TFV-positive rather than a TFV-negative result.

What is claimed is:

1. A polyclonal antibody composition comprising a heterogeneous population of mammalian antibodies that specifically bind tenofovir (TFV) and a conjugate of TFV-SH and sulfosuccinimidyl 4-(N-maleimidomethyl)cyclohexane-1-carboxylate (sulfo-SMCC) modified bovine serum albumin (BSA),
wherein the heterogeneous population of mammalian antibodies is generated against

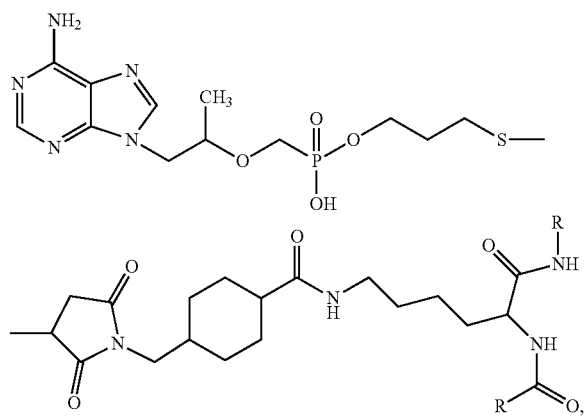

wherein R is keyhole limpet hemocyanin (KLH).

2. The composition of claim 1, wherein the heterogeneous population of mammalian antibodies is produced by immunization of a rabbit.

3. The composition of claim 1, wherein said composition is configured for detection of TFV in a test sample.

4. The composition of claim 1, wherein said composition is configured for detection of TFV in a test sample via a competition assay, a sandwich assay, a displacement assay or an electrochemical detection.

5. The composition of claim 1, wherein at least a portion of the heterogeneous population of mammalian antibodies is conjugated to a solid substrate.

6. The composition of claim 5, wherein the solid substrate is a nanoparticle.

7. The composition of claim 6, wherein the nanoparticle is a gold or silver nanoparticle.

8. The composition of claim 1, wherein at least a portion of the heterogeneous population of mammalian antibodies is immobilized on a first surface of a detection device comprising a sample pad and wherein
the sample pad is in operable fluid communication with the first surface.

9. The composition of claim 1, wherein at least a portion of the heterogeneous population of mammalian antibodies is conjugated with a detectable label.

10. A device for detecting presence of TFV in a sample, comprising:
a sample pad; and
the polyclonal antibody composition of claim 1 immobilized on a first surface; and
wherein the sample pad is in operable fluid communication with the first surface.

11. The device of claim 10, wherein the first surface is a porous surface.

12. The device of claim 10, wherein the first surface comprises nitrocellulosic material, polyvinylidene fluoride (PVDF), polyethylene material, nylon, cellulose acetate, polyester material, polyethersulfone (PES), or polysulfone.

13. The device of claim 10, wherein the device is positioned in an enclosed housing.

14. A method of detecting TFV in a test sample, comprising:
contacting the test sample with the sample pad of the device of claim 10, and
detecting binding of TFV bound with the polyclonal antibody composition immobilized on the first surface.

15. An assay for detecting the presence of tenofovir in a biological sample, comprising:
(i) contacting a biological sample with the polyclonal antibody composition of claim 1, wherein the biological sample is from a subject undergoing treatment with TFV or a compound that metabolizes to TFV; and
(ii) detecting the polyclonal antibodies bound with tenofovir.

16. The assay of claim 15, wherein the said detection comprising a competition assay, a sandwich assay, a displacement assay or an electrochemical detection.

17. The assay of claim 15, wherein said detection comprises enzyme-linked immunosorbent assay (ELISA).

18. The assay of claim 15, wherein the assay is a dipstick assay.

* * * * *